United States Patent [19]

Nestor, Jr. et al.

[11] Patent Number: 4,667,014

[45] Date of Patent: * May 19, 1987

[54] NONAPEPTIDE AND DECAPEPTIDE ANALOGS OF LHRH, USEFUL AS LHRH ANTAGONISTS

[75] Inventors: John J. Nestor, Jr., San Jose; Brian H. Vickery, Saratoga, both of Calif.

[73] Assignee: Syntex (U.S.A.) Inc., Palo Alto, Calif.

[ * ] Notice: The portion of the term of this patent subsequent to Nov. 6, 2001 has been disclaimed.

[21] Appl. No.: 495,226

[22] Filed: May 20, 1983

Related U.S. Application Data

[63] Continuation-in-part of Ser. No. 472,692, Mar. 7, 1983, Pat. No. 4,581,169, which is a continuation-in-part of Ser. No. 451,671, Dec. 21, 1982, Pat. No. 4,481,190.

[51] Int. Cl.$^4$ .................... C07K 7/20; A61K 37/28
[52] U.S. Cl. ................................. 530/313; 514/800
[58] Field of Search ............. 260/112.5 LH, 112.5 R; 514/15, 800; 530/313

[56] References Cited

U.S. PATENT DOCUMENTS

| | | | |
|---|---|---|---|
| 3,972,859 | 8/1976 | Fujino et al. | 424/177 |
| 4,215,038 | 7/1980 | Rivier et al. | 260/112.5 R |
| 4,341,767 | 7/1982 | Nestor et al. | 424/177 |
| 4,481,190 | 11/1984 | Nestor et al. | 260/112.5 R |

OTHER PUBLICATIONS

Beattie, *J. of Med. Chem.*, 18, No. 12, 1247–1250 (1975).
Kakimoto et al., *J. Biol. Chem.*, 245, 5751–55 (1970).
*Chemical Abstracts* 88, 631 (1978), Abst. No. 7331j.
Cay et al., *Endcrinalogy*, 110, No. 1, 1445–47 (1982).
Horvath et al., *Peptides*, 3, 969–971 (1982).
Walter et al., *Peptides*, Proceedings of the 4th American Symposium, Ann Arbor, Mich., 865–870 (1975).

*Primary Examiner*—Delbert R. Phillips
*Attorney, Agent, or Firm*—Ellen J. Wise; Tom M. Moran; Alen M. Krubiner

[57] ABSTRACT

Synthetic nonpeptide and decapeptide LHRH antagonist analogs have a novel guanido-substituted, amidine, tertiary or quaternary amine water-soluble aminoacyl residue at position 6.

12 Claims, No Drawings

NONAPEPTIDE AND DECAPEPTIDE ANALOGS OF LHRH, USEFUL AS LHRH ANTAGONISTS

BACKGROUND OF THE INVENTION

Luteinizing hormone (LH) and follicular stimulating hormone (FSH) are released from the anterior pituitary gland under the control of the releasing hormone LHRH produced in the hypothalamic region. LH and FSH act on the gonads to stimulate the synthesis of steroid hormones and to stimulate gamete maturation. The pulsatile release of LHRH, and thereby the release of LH and FSH, controls the reproductive cycle in domestic animals and humans.

LHRH also affects the placenta, and the gonads indirectly, in causing the release of chorionic gonadotropin (hCG).

Antagonists of LHRH are useful for the control of fertility. Such antagonists block ovulation in the female and suppress spermatogenesis in the male. Related to these effects is a suppression of normal circulating levels of sexual steroids of gonadal origin, including reduction in accessory organ weight in the male and the female. In domestic animals this effect promotes weight gain in a feed-lot situation, stimulates abortion in pregnant animals and in general, acts as a chemical sterilant.

The natural hormone releasing hormone LHRH is a decapeptide comprised of naturally occuring amino acids (which have the L-configuration except for the achiral amino acid glycine). Its sequence is as follows:

(pyro)

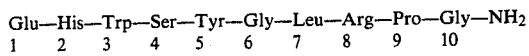

Glu—His—Trp—Ser—Tyr—Gly—Leu—Arg—Pro—Gly—NH$_2$
1    2    3    4    5    6    7    8    9    10

Many analogs of this natural material have been studied and the very large majority of them have proven to be of insufficient biological activity to be clinically useful. Certain select modifications have proven to have an agonist effect on biological activity. By far the most significant enhancement is obtained by changing the 6-position residue from Gly to a D-amino acid.

In addition to agonists, analogs have been prepared which are competitive antagonists to LHRH; all of which require deletion or replacement of the histidine residue at position 2; Vale, W., et al, *Science,* 176: 933 (1972). In general, it appears that a D-amino acid placed in the sequence at that position gives the best activity; Rees, R. W. A., et al, *J. Med. Chem.* 17: 1016 (1974).

It has also been shown that adding a modification at the 6 position, which, without the modification at position 2, results in the agonist activity cited above, enhances the antagonist activity of the 2-modified analogs; Beattie, C. W., et al, *J. Med. Chem.,* 18: 1247 (1975); Rivier, J., et al, *Peptides* 1976 p. 427, Editions de l'Universite de Bruxelles, Belgium (1976).

Against the background of these two major alterations, which result in a potent series of LHRH antagonists; additional increments in antagonist activity may be had by modifying positions 1, 3 and/or 10 in the already 2, 6 modified peptide. Coy, D. H., et al *Peptides* 1976, p. 462, Editions de l'Universite de Bruxelles, Belgium (1976); Rivier, J. E., et al, *Life Sci.* 23: 869 (1978); Dutta, A. S., et al, *Biochem Biophys. Res. Commun.* 81: 382 (1978), Humphries, J., et al, *Biochem. Biophys. Res. Commun.,* 85: 709 (1978). It has also been shown that N-acylation of the amino acid at position 1 is helpful; Channabasavaia, K., et al, *Biochem. Biophys. Res. Commun.* 81: 382 (1978); Coy, D. H., et al, *Peptides.—Structure and Biological Function* p. 775, Pierce Chemical Co. (1979). Additionally, (N-Ac-D-p-Cl-Phe$^1$, D-p-Cl-Phe$^2$, D-Trp$^3$, D-Arg$^6$, D-Ala$^{10}$)LHRH has been published by D. H. Coy, Endocrinology, 110, 1445 (1982). In another instance D-Ala$^4$ modification to LHRH has been reported to retain antagonist activity. See E. Pedroza, J. A. Martinez, D. H. Coy, A. Arimura and A. V. Schally; Int. J. Fert.; 23, 294 (1978).

Since antagonists function by competing with LHRH for the appropriate receptors, high dosages of these compounds are required in order to block out the natural peptide. It is especially desirable, in view of this, to obtain antagonists with a very high degree of potency and prolonged activity. The ability to be slowly released from depot formulations will also be important. The presently known set of analogs requires comparatively high levels of compound, with the attendant problems of increased possibility for toxicity and other side effects.

SUMMARY OF THE INVENTION

The present invention refers to novel, highly potent nonapeptide and decapeptide analogs of LHRH in which a replacement at position 2, (thus converting the peptide to the antagonist series) is made more effective by replacement of the glycine residue at position 6 by a novel guanido-substituted, amidine, or tertiary or quaternary amine water soluble amino acid residue which does not occur in nature. Further enhancements by substitutions at 1, 2, 3, 4, 7 and/or 10 are also disclosed. The invention is also directed to various methods of use of these compounds and to pharmaceutical compositions therefor. A further aspect of the invention involves processes for the preparation of the novel compounds described above.

DETAILED DESCRIPTION OF THE INVENTION

Description of the Analogs

The present invention relates to novel nonapeptide and decapeptide analogs of LHRH which have the formula

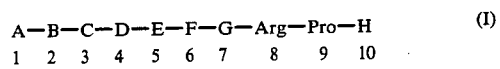

A—B—C—D—E—F—G—Arg—Pro—H    (I)
1  2  3  4  5  6  7   8    9   10 and the pharmaceutically acceptable salts thereof, wherein:

A is an amino acyl residue selected from the group consisting of L-pyroglutamyl, D-pyroglutamyl, N-acyl-D,L-tryptophanyl, N-acyl-glycyl, N-Ac-D,L-Δ$^{3,4}$-prolyl, N-Ac-D,L-prolyl, N-Ac-L-alkylprolyl, N-Ac-D,L-phenylalanyl, N-Ac-D,L-p-chlorophenylalanyl, N-Ac-D,L-seryl, N-Ac-D,L-threonyl, N-Ac-D,L-alanyl, 3-(1-naphthyl)-D,L-alanyl, 3-(2-naphthyl)-D,L-alanyl, 3-(2,4,6-trimethylphenyl)-D,L-alanyl, 3-(4-trifluoromethylphenyl)-D,L-alanyl, 3-(9-anthryl)-D,L-alanyl, 3-(2-fluorenyl)-D,L-alanyl, and 3-(Het)-D,L-alanyl wherein Het is a heterocyclic aryl containing radical selected from

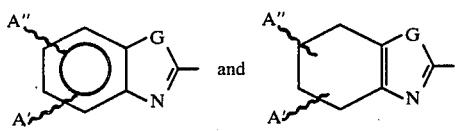 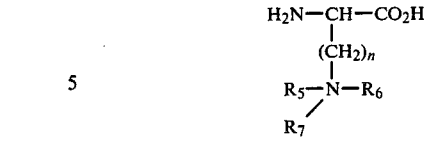

wherein
A″ and A′ are independently selected from the group consisting of hydrogen, lower alkyl, chlorine and bromine, and G is selected from the group consisting of oxygen, nitrogen and sulfur;

B is an amino acyl residue selected from the group consisting of D-phenylalanyl, D-p-Cl-phenylalanyl, D-p-F-phenylalanyl, D-p-nitrophenylalanyl, 3-(3,4,5-trimethoxyphenyl)-D-alanyl, 2,2-diphenylglycine, D-α-methyl-p-Cl-phenylalanine and 3-(2,4,6-trimethylphenyl)-D-alanyl;

C is an amino acyl residue selected from the group consisting of L-tryptophanyl, D-tryptophanyl, D-phenylalanyl, D-Me phenylalanyl, 3-(2-pyridyl)-D-alanyl, 3-(3-pyridyl)-D-alanyl, 3-(4-pyridyl)-D-alanyl, 3-(1-naphthyl)-D-alanyl, and 3-(2-naphthyl)-D-alanyl;

D is an amino acyl residue selected from the group consisting of L-seryl, and D-alanyl;

E is an amino acyl residue selected from the group consisting of L-phenylalanyl and L-tyrosyl;

F is an amino acyl selected from the group consisting of the radicals represented by the following structural formulas:

(a)

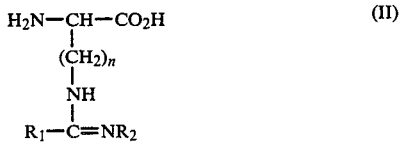

wherein
n is 1 to 5;
$R_1$ is alkyl of 1 to 12 carbon atoms, —$NRR_3$ wherein R is hydrogen or alkyl of 1 to 4 carbon atoms, $R_3$ is alkyl of 1 to 12 carbon atoms, cycloalkyl, phenyl, benzyl, —$(CH_2)_n$-morpholino or —$(CH_2)_nN(R_4)_2$ wherein n is 1 to 5 and $R_4$ is lower alkyl;

$R_2$ is hydrogen or $R_3$; or $R_1$ and $R_2$ comprise a ring represented by the following structural formulas:

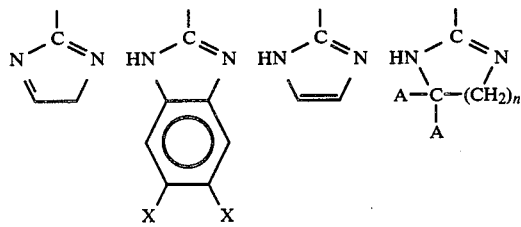

wherein n is 1 to 7; A is hydrogen, alkyl of 1 to 6 carbon atoms or cycloalkyl; and X is halo or A or (b)

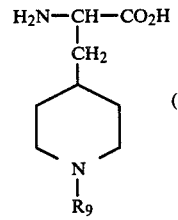

wherein $R_5$ is alkyl of 1 to 6 carbon atoms, benzyl, phenylethyl, cyclohexyl, cyclopentyl; and $R_6$ and $R_7$ are hydrogen or alkyl of 1 to 4 carbon atoms; and n is the integer 2–5; or (c) a substituent of the formula

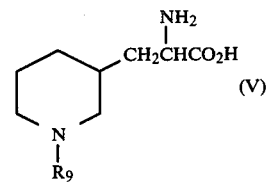

wherein
$R_9$ is hydrogen, alkyl of 1 to 12 carbon atoms, phenyl or phenylloweralkyl;

G is an amino acyl residue selected from the group consisting of L-leucyl, L-norleucyl and L-norvalyl;

H is D-alaninamide, D-leucinamide, glycinamide or —$NHR_5$ wherein $R_5$ is lower alkyl, cycloalkyl, fluoro lower alkyl, or NHCONH—$R_{10}$ wherein $R_{10}$ is hydrogen or lower alkyl; and the pharmaceutically acceptable salts thereof.

The present invention includes novel nonapeptide and decapeptide analogs of LHRH which have the formula

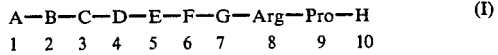

and and the pharmaceutically acceptable salts thereof, wherein:

A is an amino acyl residue selected from the group consisting of N-Ac-D,L-$\Delta^{3,4}$-prolyl, N-Ac-D,L-prolyl, N-Ac-L-alkylprolyl, N-Ac-D,L-phenylalanyl, N-Ac-D,L-p-chlorophenylalanyl, N-Ac-D,L-seryl, N-Ac-D,L-threonyl, N-Ac-D,L-alanyl, 3-(1-naphthyl)-D,L-alanyl, 3-(2-naphthyl)-D,L-alanyl, 3-(2,4,6-trimethylphenyl)-D,L-alanyl, and 3-(4-trifluoromethylphenyl)-D,L-alanyl;

B is an amino acyl residue selected from the group consisting of D-phenylalanyl, D-p-Cl-phenylalanyl, D-p-F-phenylalanyl, D-p-nitrophenylalanyl, 3-(3,4,5-trimethoxyphenyl)-D-alanyl, 2,2-diphenylglycine, D-α-methyl-p-Cl-phenylalanine and 3-(2,4,6-trimethylphenyl)-D-alanyl;

C is an amino acyl residue selected from the group consisting of D-tryptophanyl, D-phenylalanyl, D-Me$_5$-phenylalanyl, 3-(3-pyridyl)-D-alanyl, 3-(1-naphthyl)-D-alanyl, and 3-(2-naphthyl)-D-alanyl;

D is an amino acyl residue selected from the group consisting of L-seryl, and D-alanyl;

E is an amino acyl residue selected from the group consisting of L-phenylalanyl and L-tyrosyl;

F is an amino acyl selected from the group consisting of the radicals represented by the following structural formulas:

(a)

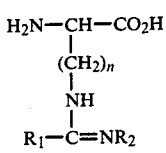

(II)

wherein
n is 1 to 5;
$R_1$ is alkyl of 1 to 12 carbon atoms, —$NHR_3$ wherein $R_3$ is alkyl of 1 to 12 carbon atoms, cycloalkyl, phenyl, benzyl, morpholino or —$(CH_2)_nN(R_4)_2$ wherein n is 1 to 5 and $R_4$ is lower alkyl;
$R_2$ is hydrogen or $R_3$; or $R_1$ and $R_2$ comprise a ring represented by the following structural formulas:

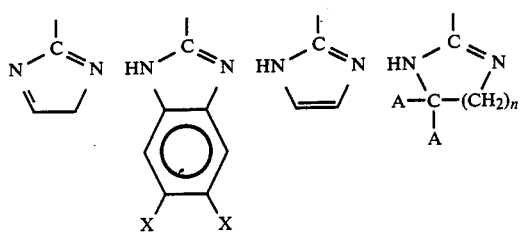

wherein n is 1 to 7; A is hydrogen, alkyl of 1 to 6 carbon atoms or cycloalkyl; and X is halo or A or (b)

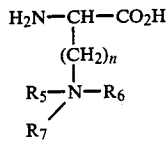

(III)

wherein $R_5$ is alkyl of 1 to 6 carbon atoms, benzyl, phenylethyl, cyclohexyl, cyclopentyl; and $R_6$ and $R_7$ are hydrogen or methyl; and n is the integer 2–5; or (c) a substituent of the formula

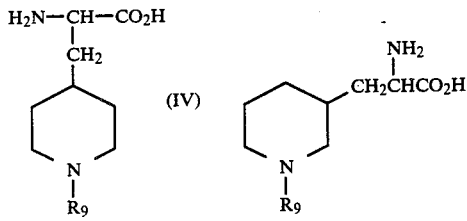

wherein $R_9$ is hydrogen, alkyl of 1 to 12 carbon atoms, phenyl or phenylloweralkyl;

G is an amino acyl residue selected from the group consisting of L-leucyl, L-norleucyl and L-norvalyl;

H is D-alaninamide, D-leucinamide, glycinamide or —$NHR_5$ wherein $R_5$ is lower alkyl or $NHCONH_2$; and the pharmaceutically acceptable salts thereof.

The replacement of the L-histidyl residue which is at position 2 in LHRH with one of the residues herein specified is a requirement to convert the peptide to an LHRH antagonist. The replacement of the glycyl residue at position 6 in LHRH with one of the residues specified as F gives a dramatic enhancement of the antagonist effect. The substitutions disclosed herein at positions 1, 2, 3, 4, 7 and 10 are further helpful in enhancing the antagonist activity.

Abbreviations and Definitions

As set forth above, and for convenience in describing this invention, the conventional abbreviations for the various common amino acids are used as generally accepted in the peptide art as recommended by the IUPAC-IUB Commission on Biochemical Nomenclature, *Biochemistry*, 11, 1726 (1972). These represent L-amino acids, with the exception of the achiral amino acid glycine, and with the further exception of any unnatural or natural amino acids which are achiral, or are otherwise designated as D-, and of those amino acids which are substituted herein into positions 1, 2, 3, 4, 6, 7 and 10 for those normally found in LHRH. All peptide sequences mentioned herein are written according to the generally accepted convention whereby the N-terminal amino acid is on the left and the C-terminal amino acid is on the right.

Certain other abbreviations will be useful in describing the invention. The present invention employs replacements by amino acids which do not occur in nature. Particularly commonly employed among these are the following:

| Amino acid residue | Abbreviation |
|---|---|
| 3-(2-naphthyl)-D-alanyl | D-Nal(2) |
| 3-(p-fluorophenyl)-D-alanyl | D-p-F-Phe |
| 3-(p-chlorophenyl)-D-alanyl | D-p-Cl-Phe |
| 3-(2,3,4,5,6-pentamethylphenyl)-D-alanyl | D-Me$_5$Phe |
| 3-(2,4,6-trimethylphenyl)-D-alanyl | D-Tmp |
| 3-(3,4,5-trimethoxyphenyl)-D-alanyl | D-Tmo |
| 3-(4-(trifluoromethylphenyl)-D-alanyl | D-Ptf |
| N,N'—guanido-dimethyl-D-homoarginine | D-Dmh |
| N,N'—guanido-diethyl-D-homoarginine | D-Deh |
| N,N'—guanido-dipropyl-D-homoarginine | D-Dph |
| N,N'—guanido-diisopropyl-D-homoarginine | D-Dih |
| N,N'—guanido-dihexyl-D-homoarginine | D-Dhh |
| N—guanido-isopropyl-D-homoarginine | D-Iph |
| N—guanido-heptyl-D-homoarginine | D-Hha |
| N—guanido-propyl-D-homoarginine | D-Prh |
| N,N'—guanido-dicyclohexyl-D-homoarginine | D-Dch |
| N,N'—guanido-diisopropyl-D-arginine | D-Dia |
| N,N'—guanido-dicyclohexyl-D-arginine | D-Dca |
| N—guanido-(3-dimethylaminopropyl)-N'—guanido-ethyl-D-homoarginine | D-Aph |
| N—guanido-(3-dimethylaminopropyl)-N'—guanido-ethyl-D-arginine | D-Apa |
| 3-(3-piperidyl)-D-alanine | D-3-Pia |
| 3-(4-piperidyl)-D-alanine | D-4-Pia |
| 3-((N$^\epsilon$—methyl)piperid-4-yl)-D-alanine | D-Mpa |
| 3-((N$^\epsilon$—pentyl)piperid-4-yl)-D-alanine | D-Ppa |
| 3-((N$^\epsilon$—benzyl)piperid-4-yl)-D-alanine | D-Bpa |
| D-N—epsilondihydroimidazolinyllysine | D-Dhi |
| 3-(2-pyridyl)-D-alanyl | D-2Pal |
| 3-(3-pyridyl)-D-alanyl | D-3Pal |
| 3-(4-pyridyl)-D-alanyl | D-4Pal |

As a further convenience, since the amino acid sequence of LHRH has been shown to be nona- and decapeptides in which the amino acid residues at particular places in the sequence have been replaced by other amino acid residues or other moieties are abbreviated by showing the nature of the substitution, superscribed by the location, followed by LHRH as the parent.

Thus, for example, the sequence,

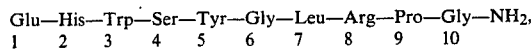

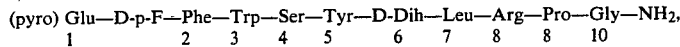

in which the Gly at position 6 has been replaced by D-Dih and the His at position 2 has been replaced by D-p-F-Phe, is represented [D-p-F-Phe², D-Dih⁶]LHRH; and the sequence

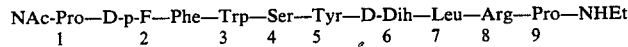

is represented: [NAc-Pro¹, D-p-F-Phe², D-Dih⁶, Pro⁹-NHEt]LHRH.

As used herein, the term "pharmaceutically acceptable salts" refers to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or with an organic cation formed from N,N'-dibenzylethylene-diamine or ethylenediamine; or of (a) and (b), e.g., a zinc tannate salt and the like.

The term "lower alkyl" refers to a straight or branched chain saturated hydrocarbon group having from 1 to 4 carbon atoms such as, for example, methyl, ethyl, n-propyl, isopropyl, n-butyl, isobutyl, sec-butyl and tert-butyl. "Alkyl of 1 to 6 carbon atoms" encompasses the same substituents as lower alkyl but in addition may have 5 or 6 carbon atoms such as, for example, a n-pentyl, n-hexyl or other branched 5 or 6 carbon membered moiety. "Alkyl of 1 to 12 carbon atoms" comprises a radical of 1 to 12 carbon atoms and hydrogen only as noted above, except that the radical may have up to 12 carbon atoms. The term "cycloalkyl" refers to a cyclic saturated hydrocarbon group having from 3 to 6 carbon atoms, for example, cyclopropyl, cyclobutyl, cyclopentyl and cyclohexyl.

For the purpose of this invention the abbreviation "alkylPro" refers to cis-5-alkyl-L-prolyl residue wherein alkyl is the same as "lower alkyl" defined above. More specifically "MePro" is cis-5-methyl-L-Prolyl, "EtPro" is cis-5-ethyl-L-Prolyl and "ButPro" is cis-5-n-butyl-L-Prolyl.

The abbreviation "N-Ac" refers specifically to the N-acetyl amino acid residue in conformance with generally accepted nomenclature.

Preferred Embodiments of the Compounds

Compounds which are preferred embodiments of the present invention are those wherein A is N-Ac-L-Pro, N-Ac-D-Ser, N-Ac-D-p-Cl-Phe, N-Ac-D-Nal(2); B is D-p-F-Phe or D-p-Cl-Phe; C is D-Trp, D-Nal(2), D-3Pal or D-Phe; D is Ser; E is Tyr; F is the compound of Formula II wherein n is 3 or 4, $R_1$ is alkyl of 1 to 8 carbon atoms or cyclohexyl and $R_2$ is hydrogen, or a compound of Formula II wherein $R_1$ is —$NHR_3$ wherein $R_3$ is methyl, ethyl, n-propyl, isopropyl, n-hexyl or cyclohexyl and $R_2$ is $R_3$ or hydrogen, or F is a compound of formula II wherein $R_1$ and $R_2$ are dihydroimidazolinyl or F is a compound of Formula (IV) or (V) wherein $R_9$ is hydrogen, methyl, pentyl or benzyl; and H is D-AlaNH₂, GlyNH₂ or NHEt.

Generally speaking, compounds wherein F is N,N'-guanido-disubstituted-D-argininyl or D-homoargininyl are among the preferred embodiments.

More preferred embodiments herein are:
A is N-Ac-L-Pro, N-Ac-D-Nal(2) or N-Ac-D-p-Cl-Phe, B is D-p-F-Phe or D-p-Cl-Phe, C is D-Nal(2), D-Trp, D-3Pal or D-Phe, D is Ser, E is Tyr, F is D-Dmh, D-Deh, D-Dph, D-Dhh or D-Dhi and H is D-AlaNH₂ GlyNH₂ or NHEt;

N-Ac-L-Pro-D-p-F-Phe-D-Nal(2)-Ser-Tyr-F-Leu-Arg-Pro-GlyNH₂, wherein F is D-Dmh, D-Deh, D-Dph, D-Dhh, D-Dhi, D-Prh or D-Hha;

N-Ac-L-Pro-D-p-Cl-Phe-D-Trp-Ser-Tyr-F-Leu-Arg-Pro-NHEt, wherein F is D-Dmh, D-Deh, D-Dph, D-Dhh, D-Dhi, D-Prh or D-Hha;

N-Ac-D-p-Cl-Phe-D-p-Cl-Phe-D-Trp-Ser-Tyr-F-Leu-Arg-Pro-D-AlaNH₂, wherein F is D-Dmh, D-Deh, D-Dph, D-Dhh, D-Dhi, D-Prh or D-Hha;

N-Ac-D-p-Cl-Phe-D-p-Cl-Phe-D-Trp-Ser-Tyr-F-Leu-Arg-Pro-GlyNH₂, wherein F is D-Dmh, D-Deh, D-Dph, D-Dhh, D-Dhi, D-Prh or D-Hha; and N-Ac-D-Nal(2)-D-p-F-Phe-D-Trp-Ser-Tyr-F-Leu-Arg-Pro-GlyNH₂, wherein F is D-Dmh, D-Deh, D-Dph, D-Dhh, D-Dhi, D-Prh, D-Hha or propyl amidine.

N-Ac-D-Nal(2)-D-p-Cl-Phe-D-Trp-Ser-Tyr-F-Leu-Arg-Pro-GlyNH₂, wherein F is D-Dmh, D-Deh, D-Dph, D-Dhh or D-Dhi;

N-Ac-D-Nal(2)-D-p-Cl-Phe-D-Trp-Ser-Tyr-F-Leu-Arg-Pro-D-AlaNH₂, wherein F is D-Dmh, D-Deh, D-Dph, D-Dhh or D-Dhi;

N-Ac-D-Nal(2)-D-p-Cl-Phe-D-3Pal-Ser-Tyr-F-Leu-Arg-Pro-GlyNH₂, wherein F is D-Dmh, D-Deh, D-Dph, D-Dhh or D-Dhi;

N-Ac-D-Nal(2)-D-p-Cl-Phe-D-3Pal-Ser-Tyr-F-Leu-Arg-Pro-D-AlaNH₂, wherein F is D-Dmh, D-Deh, D-Dph, D-Dhh or D-Dhi.

The most particularly preferred embodiments are:

N-Ac-L-Pro-D-p-F-Phe-D-Trp-Ser-Tyr-D-Deh-Leu-Arg-Pro-NHEt;
N-Ac-L-Pro-D-p-F-Phe-D-Trp-Ser-Tyr-D-Dph-Leu-Arg-Pro-NHEt;
N-Ac-L-Pro-D-p-F-Phe-D-Trp-Ser-Tyr-D-Dhh-Leu-Arg-Pro-NHEt;
N-Ac-D-Nal(2)-D-p-F-Phe-D-Trp-Ser-Tyr-D-Deh-Leu-Arg-Pro-NHEt;
N-Ac-D-Nal(2)-D-p-Cl-Phe-D-Trp-Ser-Tyr-D-Deh-Leu-Arg-Pro-NHEt;
N-Ac-D-Nal(2)-D-p-F-Phe-D-Trp-Ser-Tyr-D-Dmh-Leu-Arg-Pro-GlyNH$_2$;
N-Ac-D-Nal(2)-D-p-F-Phe-D-Trp-Ser-Tyr-D-Deh-Leu-Arg-Pro-GlyNH$_2$;
N-Ac-D-Nal(2)-D-p-F-Phe-D-Trp-Ser-Tyr-D-Dph-Leu-Arg-Pro-GlyNH$_2$;
N-Ac-D-Nal(2)-D-p-F-Phe-D-Trp-Ser-Tyr-D-Dhh-Leu-Arg-Pro-GlyNH$_2$;
N-Ac-D-Nal(2)-D-p-F-Phe-D-Trp-Ser-Tyr-D-Dhi-Leu-Arg-Pro-GlyNH$_2$;
N-Ac-D-Nal(2)-D-p-Cl-Phe-D-Trp-Ser-Tyr-D-Dmh-Leu-Arg-Pro-GlyNH$_2$;
N-Ac-D-Nal(2)-D-p-Cl-Phe-D-Trp-Ser-Tyr-D-Deh-Leu-Arg-Pro-GlyNH$_2$;
N-Ac-D-Nal(2)-D-p-Cl-Phe-D-Trp-Ser-Tyr-D-Dph-Leu-Arg-Pro-GlyNH$_2$;
N-Ac-D-Nal(2)-D-p-Cl-Phe-D-Trp-Ser-Tyr-D-Dhh-Leu-Arg-Pro-GlyNH$_2$;
N-Ac-D-Nal(2)-D-p-Cl-Phe-D-Trp-Ser-Tyr-D-Dhi-Leu-Arg-Pro-GlyNH$_2$;
N-Ac-D-Nal(2)-D-p-F-Phe-D-3Pal-Ser-Tyr-D-Deh-Leu-Arg-Pro-D-AlaNH$_2$;
N-Ac-D-Nal(2)-D-p-F-Phe-D-3Pal-Ser-Tyr-D-Deh-Leu-Arg-Pro-D-GlyNH$_2$;
N-Ac-D-p-Cl-Phe-D-p-Cl-Phe-D-3Pal-Ser-Tyr-D-Deh-Leu-Arg-Pro-D-AlaNH$_2$;
N-Ac-D-p-Cl-Phe-D-p-Cl-Phe-D-3Pal-Ser-Tyr-D-Deh-Leu-Arg-Pro-D-GlyNH$_2$;
N-Ac-D-p-Cl-Phe-D-p-Cl-Phe-D-Trp-Ser-Tyr-D-Dmh-Leu-Arg-Pro-GlyNH$_2$;
N-Ac-D-p-Cl-Phe-D-p-Cl-Phe-D-Trp-Ser-Tyr-D-Deh-Leu-Arg-Pro-GlyNH$_2$;
N-Ac-D-p-Cl-Phe-D-p-Cl-Phe-D-Trp-Ser-Tyr-D-Dph-Leu-Arg-Pro-GlyNH$_2$;
N-Ac-D-p-Cl-Phe-D-p-Cl-Phe-D-Trp-Ser-Tyr-D-Dhh-Leu-Arg-Pro-GlyNH$_2$;
N-Ac-D-p-Cl-Phe-D-p-Cl-Phe-D-Trp-Ser-Tyr-D-Dhi-Leu-Arg-Pro-GlyNH$_2$;
N-Ac-D-p-Cl-Phe-D-p-Cl-Phe-D-Trp-Ser-Tyr-D-Deh-Leu-Arg-Pro-D-AlaNH$_2$;
N-Ac-D-p-Cl-Phe-D-p-Cl-Phe-D-Trp-Ser-Tyr-D-Dph-Leu-Arg-Pro-D-AlaNH$_2$;
N-Ac-D-p-Cl-Phe-D-p-Cl-Phe-D-Trp-Ser-Tyr-D-Dhh-Leu-Arg-Pro-D-AlaNH$_2$;
N-Ac-D-Nal(2)-D-pCl-Phe-D-Trp-Ser-Tyr-D-Deh-Leu-Arg-Pro-D-AlaNH$_2$;
N-Ac-D-Nal(2)-D-p-F-Phe-D-Trp-Ser-Tyr-D-Deh-Leu-Arg-Pro-D-AlaNH$_2$;
N-Ac-D-Nal(2)-D-p-Cl-Phe-D-Trp-Ser-Tyr-D-Dmh-Leu-Arg-Pro-D-AlaNH$_2$;
N-Ac-D-Nal(2)-D-p-Cl-Phe-D-Trp-Ser-Tyr-D-Dph-Leu-Arg-Pro-D-AlaNH$_2$;
N-Ac-D-Nal(2)-D-p-Cl-Phe-D-Trp-Ser-Tyr-D-Dhh-Leu-Arg-Pro-D-AlaNH$_2$;
N-Ac-D-Nal(2)-D-p-Cl-Phe-D-Trp-Ser-Tyr-D-Dhi-Leu-Arg-Pro-D-AlaNH$_2$;
N-Ac-D-Nal(2)-D-p-Cl-Phe-D-3Pal-Ser-Tyr-D-Dmh-Leu-Arg-Pro-D-AlaNH$_2$;
N-Ac-D-Nal(2)-D-p-Cl-Phe-D-3Pal-Ser-Tyr-D-Deh-Leu-Arg-Pro-D-AlaNH$_2$;
N-Ac-D-Nal(2)-D-p-Cl-Phe-D-3Pal-Ser-Tyr-D-Dph-Leu-Arg-Pro-D-AlaNH$_2$;
N-Ac-D-Nal(2)-D-p-Cl-Phe-D-3Pal-Ser-Tyr-D-Dhh-Leu-Arg-Pro-D-AlaNH$_2$;
N-Ac-D-Nal(2)-D-p-Cl-Phe-D-3Pal-Ser-Tyr-D-Dhi-Leu-Arg-Pro-D-AlaNH$_2$;
N-Ac-D-Nal(2)-D-p-Cl-Phe-D-3Pal-Ser-Tyr-D-Dmh-Leu-Arg-Pro-GlyNH$_2$;
N-Ac-D-Nal(2)-D-p-Cl-Phe-D-3Pal-Ser-Tyr-D-Deh-Leu-Arg-Pro-GlyNH$_2$;
N-Ac-D-Nal(2)-D-p-Cl-Phe-D-3Pal-Ser-Tyr-D-Dph-Leu-Arg-Pro-GlyNH$_2$;
N-Ac-D-Nal(2)-D-p-Cl-Phe-D-3Pal-Ser-Tyr-D-Dhh-Leu-Arg-Pro-GlyNH$_2$; and
N-Ac-D-Nal(2)-D-p-Cl-Phe-D-3Pal-Ser-Tyr-D-Dhi-Leu-Arg-Pro-GlyNH$_2$.

In all of the above embodiments, the compound may also be prepared as the corresponding pharmaceutically acceptable salt.

Assay Procedures

The compounds of this invention and, particularly, the salts thereof, exhibit surprisingly potent and long lasting LHRH antagonist activity.

Primary measures of potency are ability to inhibit ovulation in rats, as assayed by the procedure of Corbin, A. and Beattie, C. W., *Endocrine Res. Commun.*, 2:1 (1975) and ability to inhibit LH release and ovulation in the rabbit, as per Phelps, C. P., et al, *Endocrinology* 100: 1526 (1977).

Other bioassays which are used for LHRH antagonists and for the compounds of the present invention are:

(a) inhibition of LHRH induced FSH and LH release in the rat, in vivo; Vilchez-Martinez, J. A., et al, *Endocrinology*, 96: 1130 (1975); and, (b) inhibition of LH and FSH release by dispersed anterior pituitary cell cultures as measured by radioimmuno assay. (Vale, W., et al, *Endocrinology* 91: 562 (1972).

Antagonist Effects and Utilities

The following utilities flow from the antagonist effect of the compounds herein:
female contraception;
ovulation suppression or delay;
induction of parturition;
synchronization of ovulation;
estrus suppression;
growth promotion in female animals;
luteolysis, menses induction;
early, first trimester abortifacient;
therapy for endometriosis;
therapy for mammary tumors and cysts
therapy for polycystic ovary syndrome (Stein-Leventhal);
therapy for uterine carcinoma;
therapy for benign prostatic hypertrophy and for prostatic carcinoma;
male contraception;
therapy for diseases which result from excessive gonadal hormone production in either sex;
functional castration in male food producing animals;
suppression of proestrous bloody discharge in dogs;
suppression of menopausal symptoms.

The aspect of the present invention which relates to particular uses for the above-described compounds is concerned with these utilities, most particularly; inhibition of ovulation and treatment of endometriosis in the female, and inhibition of spermatogenesis and treatment of prostatic tumors in the male.

In the practice of the method of this invention an effective amount of a compound of the invention or a pharmaceutical composition containing same is administered to the subject in need of, or desiring, such treatment. These compounds or compositions may be administered by any of a variety of routes depending upon the specific end use, including orally, parenterally (including subcutaneous, intramuscular and intravenous administration), vaginally (particularly for contraception), rectally, buccally (including sublingually), transdermally or intranasally. The most suitable route in any given case will depend upon the use, particular active ingredient, the subject involved, and the judgment of the medical practitioner. The compound or composition may also be administered by means of slow-release, depot or implant formulations as describe,d more fully herein below.

In general for the uses herein above described, it is expedient to administer the active ingredient in amounts between about 0.01 and 10 mg/kg body weight per day, preferably between about 0.1 and 5.0 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and, of course, the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intravenous) administration particularly in the form of liquid solutions or suspensions; for use in vaginal or rectal administration particularly in semisolid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well-known in the pharmaceutical art, for example as described in *Remington's Pharmaceutical Sciences*, Mack Publishing Company, Easton, PA., 1970. Formulations for parenteral administration may contain as common excipients sterile water or saline, polyalkylene glycols such as polyethylene glycol, oils of vegetable origin, hydrogenated naphthalenes and the like. Formulations for vaginal or rectal administration, e.g. suppositories, may contain as excipients, for example, polyalkyleneglycols, vaseline, cocoa butter, and the like. Formulations for inhalation administration may be solid and contain as excipients, for example, lactose or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of the compound which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as a polylactic acid polymer for example as described in U.S. Pat. No. 3,773,919. The compounds or, preferably, relatively insoluble salts such as those described above may also be formulated in cholesterol matrix pellets, particularly for use in animals. Additional slow release, depot or implant formulations, e.g. liposomes, are well known in the literature. See, for example, *Sustained and Controlled Release Drug Delivery Systems*, J. R. Robinson ed., Marcel Dekker, Inc., New York, 1978. Particular reference with respect to LHRH type compounds may be found, for example, in U.S. Pat. No. 4,010,125.

Synthesis of the Peptides

The polypeptides of the present invention may be synthesized by any techniques that are known to those skilled in the peptide art. An excellent summary of the many techniques so available may be found in J. M. Stewart and J. D. Young, *Solid Phase Peptide Synthesis*, W. H. Freeman Co., San Francisco, 1969, and J. Meienhofer, *Hormonal Proteins and Peptides*, Vol. 2, p. 46., Academic Press (New York), 1973 for solid phase peptide synthesis and E. Schroder and K. Lubke, *The Peptides*, Vol. 1, Academic Press (New York), 1965 for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

Preferred Embodiments of Synthesis

A particularly preferred method of preparing compounds of the present invention involves solid phase peptide synthesis.

In this particularly preferred method the α-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Cbz), biphenylisopropyloxycarbonyl, t-amyloxycarbonyl, isobornyloxycarbonyl, 1,1-dimethyl-3,5-dimethoxybenzyloxycarbonyl, o-nitrophenylsulfenyl, 2-cyano-t-butyloxycarbonyl, 9-fluorenylmethyloxycarbonyl and the like, especially t-butyloxycarbonyl (Boc).

Particularly preferred side chain protecting groups are, for arginine:nitro, p-toluenesulfonyl, 4-methoxybenzenesulfonyl, Cbz, Boc and adamantyloxycarbonyl; for tyrosine:benzyl, o-bromobenzyloxycarbonyl, 2,6-dichlorobenzyl, isopropyl, cyclohexyl, cyclopentyl and acetyl; for serine:benzyl and tetrahydropyranyl; for histidine:benzyl, p-toluenesulfonyl and 2,4-dinitrophenyl.

The C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer, and the like, especially chloromethyl-polystyrene-1% divinylbenzene polymer. For the special case where the C-terminus of the compound will be glycinamide, a particularly useful support is the benzhydrylamino-polystyrene-divinylbenzene polymer described by P. Rivaille, et al, *Helv. Chim. Acta.*, 54, 2772 (1971). The attachment to the chloromethyl polystyrene-divinylbenzene type of resin is made by means of the reaction of the $N^\alpha$-protected amino acid, especially the Boc amino acid, as its cesium, tetramethylammonium, triethylammonium, 1,5-diazabicyclo[5.4.0]undec-5-ene, or similar salt in ethanol, acetonitrile, N,N-dimethylformamide (DMF), and the like, especially the cesium salt in DMF, with the chloromethyl resin at an elevated temperature, for example between about 40° and 60° C., preferably about 50° C., for from about 12 to 48 hours, preferably about 24 hours. The $N^\alpha$-Boc-amino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° and 50° C., preferably 25° C. in a solvent such as dichloromethane or DMF, preferably dichlormethane. The coupling of successive protected amino acids can be carried out in an automatic polypeptide synthesizer as is well known in the art. The removal of the $N^\alpha$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in approximately 2.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-iso-propylcarbodiimide (DIC) or other carbodiimide either alone or in the presence of HBT, N-hydroxysuccin-imide, other N-hydroxyimides or oximes. Alternately, protected amino acid active esters (e.g. p-nitrophenyl, pentafluorophenyl and the like) or symmetrical anhydrides may be used.

At the end of the solid phase synthesis the fully protected polypeptide is removed from the resin. When the linkage to the resin support is of the benzyl ester type, cleavage is by means of aminolysis with an alkylamine or fluoroalkylamine for peptides with a proline C-terminus, or by aminolysis with, for example, ammonia/methanol or ammonia/ethanol for peptides with a glycine C-terminus at a temperature between about 10° and 50° C., preferably about 25° C., for between about 12 and 24 hours preferably about 18 hours. Alternatively, the peptide may be removed from the resin by transesterification, e.g., with methanol, followed by aminolysis. The protected peptide may be purified at this point by silica gel chromatography. The removal of the side chain protecting groups from the polypeptide is performed by treating the aminolysis product with, for example, anhydrous liquid hydrogen fluoride in the presence of anisole or other carbonium scavenger, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride, and anisole at a temperature between about −10° and +10° C., preferably about 0° C., for between about 15 minutes and 1 hour, preferably about 30 minutes. For the glycine terminal peptides on the benzyhydrylamine resins, the resin cleavage and deprotection steps may be combined in a single step utilizing liquid hydrogen fluoride and anisole as described above. The fully deprotected polypeptide is then purified by a sequence of chromatographic steps employing any or all of the following types: ion exchange on a weakly basic resin in the acetate form; hydrophobic adsorption chromatography on underivatized polystyrene-divinylbenzene (for example Amberlite XAD); silica gel adsorption chromatography; ion exchange chromatography on carboxymethylcellulose; partition chromatography, e.g., on Sephadex G-25, or countercurrent distribution; high performance liquid chromatography (HPLC), especially reverse phase HPLC on octyl- or octadecylsilyl-silica bonded phase column packing.

If a racemic amino acid is used in the 1, 2, 3 or 6 position, the diastereomeric nonapeptide or decapeptide final products are separated, and the desired peptide containing a D-amino acid in the appropriate position is isolated and purified, preferably during the above-described chromatographic process.

The preparation of peptides having C-terminal azaglycine amides is preferably done using classical peptide solution synthesis using known peptide intermediates. This is described in more detail in Example 3.

Thus, in another aspect the present invention relates to a method for preparing compounds of the invention and of the pharmaceutically acceptable salts thereof which process comprises:

removing protecting groups and, optionally, covalently bound solid support from a protected polypeptide to afford a compound of Formula (I) or a salt thereof; or coupling together in the required sequence two fragments of the desired compound of formula (I); or (a) converting a compound of Formula (I) to a pharmaceutically acceptable salt, or (b) converting a salt of a compound of Formula (I) to a pharmaceutically acceptable salt, or (c) decomposing a salt of a compound of Formula (I) to a free polypeptide of Formula (I).

It will be appreciated that the guanido-substituted, amidine, and tertiary and quaternary amine water soluble amino acids used in this invention to replace the glycine residue at position 6 of LHRH are useful intermediates and as such form an important part of this invention.

Particularly useful intermediates of this invention include those of formula (II) wherein n is 1 or 2 and the other variables are as previously defined; those of formula (II) wherein n is 3, $R_3$ is alkyl of 2 to 12 carbon atoms or as otherwise defined previously, and the other variables are as previously defined; and those of formula (II) wherein n is 4 or 5, and the other variables are as previously defined.

Preferred intermediates include those of formula (II) wherein n is 4, R is —$NRR_3$ wherein R is hydrogen and $R_3$ is alkyl of 1 to 12 carbon atoms, and $R_2$ is alkyl of 1 to 12 carbon atoms.

Such intermediates of formula (II) may be prepared in any convenient manner, an example of which is by guanylating or amidinating the corresponding amine.

The following examples are given to enable those skilled in the art to more fully understand and practice the present invention. They should not be construed as a limitation upon the scope of the invention, but merely as being illustrative and representative thereof.

PREPARATION A

N-ACETYL 3-(2-NAPHTHYL)-D,L-ALANINATE

The preparation of 3-(2-naphthyl)-D,L-alanine is carried out according to the procedure set out in U.S. Pat. No. 4,341,767.

Preparation of N acetyl 3-(2-naphthyl)-D,L-alinine, its conversion to methyl N acetyl 3-(2-naphthyl)-D,L-alinine, and separation of the D isomer is carried out by the procedure disclosed in U.S. Pat. No. 4,341,767.

PREPARATION B

A mixture of 5.24 g of benzyl $N_\alpha$-benzyloxycarbonyl-D-lysinate toluenesulfonate (B. Bezus and L. Zervas, J. Am. Chem. Soc. 83, 719 (1961)) and 1.72 ml of diisopropylethylamine in 60 ml of dioxane is treated with 1.89 g of N,N'-diisopropylcarbodiimide. The reaction mixture is stirred at 100° C. for 6 hours, cooled to room temperature and concentrated to a solid. The solid is suspended in 20 ml of warm DMF, filtered to remove N,N'-diisopropylurea and the filtrate concentrated to a solid. Benzyl $N_\alpha$-benzyloxycarbonyl-N,N'-guanidodiisopropyl-D-homoargininate toluenesulfonate is obtained as a white solid by crystallization from methanol/ethyl acetate $[\alpha]_D - 7.26°$ (C 0.3, MeOH).

Similarly, by using the above procedure, but substituting:

N,N'-dicyclohexylcarbodiimide;
N,N'-di-n-hexylcarbodiimide;
N,N'-diethylcarbodiimide;
N,N'-di-n-propylcarbodiimide;
N-i-propylcarbodiimide;
N-propylcarbodiimide;
N,N'-di-n-butylcarbodiimide;
N,N'-dimethylcarbodiimide;
N,N'-di-i-butylcarbodiimide;
N,N'-di-n-pentylcarbodiimide;
N,N'-di-i-pentylcarbodiimide;
N,N'-diphenylcarbodiimide;
N,N'-ditolylcarbodiimide; or
1-(3-dimethylaminopropyl)-3-ethylcarbodiimide-HCl and the like, there are obtained:

benzyl $N^\alpha$-benzyloxycarbonyl-N,N'-guanidodicyclohexyl-D-homoargininate, $[\alpha]_D 8.07°$ (C 0.9 MeOH);

benzyl $N^\alpha$-benzyloxycarbonyl-N,N'-guanidodiethyl-D-homoargininate;

benzyl $N^\alpha$-benzyloxycarbonyl-N,N'-guanido-di-n-propyl-D-homoargininate $[\alpha]_D 8.07°$ (C 0.9 MeOH);

benzyl $N^\alpha$-benzyloxycarbonyl-N,N'-guanido-n-propyl-D-homoargininate;

benzyl $N^\alpha$-benzyloxycarbonyl-N,N'-guanido-di-n-butyl-D-homoargininate;

benzyl $N^\alpha$-benzyloxycarbonyl-N,N'-guanido-di-i-butyl-D-homoargininate;

benzyl $N^\alpha$-benzyloxycarbonyl-N,N'-guanido-di-n-pentyl-D-homoargininate;

benzyl $N^\alpha$-benzyloxycarbonyl-N,N'-guanido-di-phenyl-D-homoargininate;

benzyl $N^\alpha$-benzyloxycarbonyl-N,N'-guanido-dimethyl-D-homoargininate;

benzyl $N^\alpha$-benzyloxycarbonyl-N,N'-guanido-di-n-hexyl-D-homoargininate;

benzyl $N^\alpha$-benzyloxycarbonyl-N,N'-guanido-di-isopropyl-D-argininate, $[\alpha]_D - 10.5°$ (C 0.5, MeOH);

benzyl $N^\alpha$-benzyloxycarbonyl, N-guanido-(3-dimethylaminopropyl)-N'-guanido-ethyl-D-homoargininate as their benzenesulfonate salts. Similiarly, by substituting benzyl $N^\alpha$-benzyloxycarbonyl-D-ornithinate for the D-lysinate there may be obtained the corresponding arginine analogs as their toluenesulfonate salts.

PREPARATION C

(i) Benzyl $N^\alpha$-benzyloxycarbonyl-$N^G,N^{G'}$-ethano-D-homoargininate To a mixture of 15 ml of toluene and 15 ml of t-BuOH was added 2.71 g of benzyl $N^\alpha$-benzyloxycarbonyl-D-lysinate and 1.46 g of 2-methylthioimidazoline.HI (available from Aldrich). The pH of the mixture was brought to ~8 by the addition of diisopropylethylamine and the solution heated under reflux for 24 hours.

The solution was concentrated in vacuo and the residue was loaded on a silica gel column (250 g). The column was eluted with a gradient from $CH_2Cl_2$/MeOH (19:1) to $CH_2Cl_2$/MeoH (7:3). The fractions containing product were detected by TLC, pooled, and concentrated to dryness, 2.9 g of white foam.

A 2 g portion of the above-named product was dissolved in 50 ml of EtOH containing 0.8 g of 10% Pd/C. The solution was stirred under $H_2$ for 8 hours. The mixture was filtered on celite and the filtrate was concentrated to dryness to give $N^G,N^{G'}$-etheno-D-homoarginine as a white foam, 1.2 g.

(ii) $N^\alpha$-Boc-$N^G,N^{G'}$-ethano-D-homoarginine

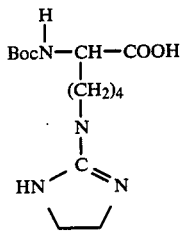

A solution of 2.74 g of D-lysine dihydrochloride and 4.03 g of 2-methylthio-2-imidazoline.hydroiodide in 16.5 ml of 2N NaOH was stirred at room temperature for 6 days. Analysis of the reaction mixture on an amino acid analyzer showed that ~70% of the desired ε-dialkylguanido compound had been formed. A further 0.25 g of the 2-methylthio-2-imidazoline.hydroiodide and 1 ml of 2N NaOH were added and the reaction was continued at room temperature for 3 more days.

The reaction mixture was treated with 0.8 g MgO and 4.36 g of di-tert-butyldicarbonate in 20 ml of dioxane. The pH was adjusted to 9.5 with 1N NaOH. After overnight reaction some starting material was present, so 1 g of di-tert-butyldicarbonate was added.

The mixture was filtered and the filtrate was concentrated to dryness. The residue was dissolved in $H_2O$ and washed with $Et_2O$ and the aqueous layer was adjusted to pH 4 with HOAc. The acidic solution was washed with EtOAc. The aqueous layer containing the product was treated with anion exchange resin (AG-3 acetate, BioRad) and concentrated to dryness.

The crude product was passed through a hydrophobic chromatography column (Amberlite XAD-2, Rohm & Haas) by elution with a gradient from $H_2O$ to 25% EtOH. The fractions containing product were pooled to yield 2.7 g of $N^\alpha$-Boc-$N^G,N^{G'}$-ethano-D-homoarginine, $[\alpha]_D^{25} -19.7°$ (c 0.1, MeOH).

In a similar fashion, by substituting:
S-methyl-diethyl-iso-thiourea-HI,
S-methyl-dipropyl-iso-thiourea-HI,
S-methyl-dibutyl-iso-thiourea-HI,
S-methyl-dipentyl-iso-thiourea-HI,
S-methyl-dihexyl-iso-thiourea-HI,
S-methyl-diheptyl-iso-thiourea-HI, and
S-methyl-dinonyl-iso-thiourea-HI
for 2-methylthio-2-imidazoline-HI, there are obtained:
$N^\alpha$-Boc-N,N'-guanido-diethyl-D-homoarginine,
$N^\alpha$-Boc-N,N'-guanido-dipropyl-D-homoarginine,
$N^\alpha$-Boc-N,N'-guanido-dibutyl-D-homoarginine,
$N^\alpha$-Boc-N,N'-guanido-dipentyl-D-homoarginine,
$N^\alpha$-Boc-N,N'-guanido-dihexyl-D-homoarginine,
$N^\alpha$-Boc-N,N'-guanido-diheptyl-D-homoarginine, and
$N^\alpha$-Boc-N,N'-guanido-dinonyl-D-homoarginine.

PREPARATION D

This Preparation illustrates the preparation of $N^\alpha$-t-butyloxy carbonyl derivatives of N,N'-guanido-disubstituted-D-homoarginines from their toluenesulfonate precursors.

A mixture of N,N'-guanido-diisopropyl-D-homoargininate toluenesulfonate (3.25 g) and 100 mg of 10% Pd/C in 50 ml of glacial acetic acid is treated with hydrogen gas at atmospheric pressure for 4 hours. The catalyst is filtered on celite and the filtrate is concentrated to a solid, N,N'-guanido-diisopropyl-D-homoarginine toluenesulfonate. A solution of this compound (2.13 g) in 60 ml of 50% dioxane/water is treated with 10 ml of 1N sodium hydroxide and 0.4 g of magnesium oxide. This mixture is then treated with 1.1 g of di-t-butyldicarbonate and stirred at room temperature for 2 hours. The magnesium salt is filtered and the filtrate is concentrated under vacuum. The basic solution is washed with ethanol, then brought to pH 2.5 with sodium sulfate. The acidic aqueous solution is extracted with ethylacetate which is dried over magnesium sulfate. The drying agent is filtered and the filtrate is concentrated. Crystallization from ethyl acetate/hexane affords $N^\alpha$-t-butyloxycarbonyl,N,N'-guanido-diisopropyl-D-homoarginine toluenesulfonate.

Proceeding in a similiar manner, but substituting the appropriate toluenesulfonate precursors, other $N^\alpha$-t-butyloxycarbonyl-N,N'-guanido-disubstituted-D-homoarginine or D-arginine compounds may be prepared.

PREPARATION E $N_\alpha$-t-butyloxycarbonyl-3-(4'-(1'-propylpiperidyl))-D-alanine A 4.6 g portion of sodium metal was added to 400 ml of absolute ethanol and heated. To the resultant solution of sodium ethoxide was added 21.7 g of diethyl acetamidomalonate and 16.4 g of 4-picolyl chloride hydrochloride (Aldrich Chem. Co.). The reaction mixture was heated to 100° C. for 4 hours, cooled, filtered and concentrated in vacuo. The mixture was loaded on a silica gel column in methylene chloride/methanol (19:1) and eluted with the same mixture. The product was located as a fast running UV positive spot by TLC on silica gel in methylene chloride/methanol (19:1). Combined fractions were concentrated to provide the product.

The product from the foregoing paragraph was dissolved in 200 ml of ethanol and treated with a solution of 2.72 g of sodium hydroxide in 40 ml of water at 50° C. for 6 hours. The solution was acidified with 12 ml of 6N HCl, concentrated to dryness and taken up in 200 ml of dioxane. The suspension was filtered and the filtrate heated at reflux for 2 hours. The solution was cooled and concentrated to dryness to yield ethyl $N^\alpha$-acetyl-3-(4-pyridyl)-D,L-alanine as a white solid.

A portion of this N-acetyl ester was resolved by treatment with 200 ml of the enzyme subtilisin Carlsberg (Sigma Chem. Co., protease VIII) in a mixture of 300 ml of dimethyl sulfoxide and 400 ml of 0.01M KCl (pH 7.2). The pH was maintained by addition of 1N NaOH on a pH stat. After a 6 hour period, the resolution was complete. The solution was diluted with 400 ml of water and extracted with 4×750 ml of ethyl acetate. The organic layers were combined and dried over magnesium sulfate and concentrated to yield ethyl $N^\alpha$-acetyl-3-(4-pyridyl)-D-alaninate as an oil.

The oil was reacted with 1.22 g of n-propyl bromide in 50 ml of ethanol after which the solution was concentrated to dryness to yield ethyl $N^\alpha$-acetyl-3-(1-propylpyridinium-4-yl)-D-alininate bromide as a white hygroscopic solid.

This white solid was dissolved in 200 ml of ethanol and was reduced under an atmosphere of hydrogen gas using 100 mg of 10% Pd/C as a catalyst. After an 18 hour reduction period, the catalyst was filtered out and the solutin concentrated to yield ethyl $N^\alpha$-acetyl-3-(4'-(1'-propylpiperidyl))-D-alininate as a tan solid. The free acid was prepared by refluxing the ethyl ester in 100 ml of 6N HCl for 4 hours to yield 3-(4'-(1'-propyl-piperidyl))-D-alanine as a white solid.

The free acid was dissolved in 100 ml of dioxane/water (1:1) and treated with 2 g of di-t-butyldicarbonate. The pH was maintained at 9 by addition of 1N NaOH on a pH stat. After 2 hours the reaction muxture was concentrated in vacuo, washed wtih 100 ml of ethyl ether and the aqueous laye was loaded on an Amberlite XAD-2 hydrophobic resin. The column was eluted with 250 ml of water followed by 250 ml of 50% ethanol/ater. The ethanol eluate was pooled and concentrated to dryness to yield $N^\alpha$-t-butyloxy-carbonyl-3-(4'-(1'-propylpiperidyl))-D-alanine as a white solid.

Proceeding in similiar manner, but substituting 3-picolyl chloride hydrochloride for 4-picolyl chloride hydrochloride, there is prepared $N^\alpha$-t-butyloxy-carbonyl-3-(3'-(1'-propylpiperidyl))-D-alanine.

PREPARATION F

Cis-5-alkylproline compounds may be prepared by the following method:

To a 200-ml round-bottomed flask is added (S)-3-(benzyloxycarbonyl)-5-oxo-4-oxazolidinepropionic acid and 63 ml of anhydrous benzene. To this solution is added 13.9 g of phosphorus pentachloride at 0° C. The reaction mixture is stirred at 0° C. for 1 hr during which time all of the phosphorus pentachloride dissolves. The benzene solvent is removed under vacuum and co-evaporation with two 25 ml samples of dry benzene, and the residue dried under vacuum to give a light solid. The light solid is suspended in 30 ml of hexamethylphosphoramide and 9.4 ml of tetramethyltin and 40 mg of $PhCH_2Pd(PPh_3)_2Cl$ is added. The reaction mixture is heated at 65° C. for 4 hours. An additional 2 ml of tetramethyltin is added at the end of that period and the reaction mixture is stirred over night at room temperature. After dilution with water and extraction with ethyl acetate, the ethyl acetate layer is washed with water, 5% sodium bicarbonate, water, 5% sodium bisulfate, water, and saturated sodium chloride and dried over anhydrous magnesium sulfate. The solution is filtered and concentrated to give 16 g of a yellow oil, which is passed through a silica gel column using ethyl acetate/hexane(4/6) as eluent. Concentration of the appropriate fractions gives 15 g of a light yellow oil which is recrystallized from ethyl acetate-hexane to produce 14.3 g of (S)-3-(benzyloxycarbonyl)-4-(3-oxobutyl)-5-oxazolidinone as a white solid (74% yield), having a mp of 64°-65° C., $[\alpha]_D^{25} = +102°$ (c=1.1, $CH_2Cl_2$).

Anal: Calcd. for $C_{18}H_{17}NO_5$: C, 61.85; H, 5.84; N, 4.81. Found: C, 61.54; H, 5.89; N, 4.84.

By repeating the above procedure in a similar manner, and, by replacing the tetramethyltin with a stoichiometrically equivalent of the appropriate tetraalkyltin the following compounds are prepared:

(a) With tetraethyltin (S)-3-(Benzyloxycarbonyl)-4-(3-oxopentyl)-5-oxazolidinone having a mp of 45°–46° C.;
$[\alpha]_D^{25}=82.5°$ (c 0.7, $CH_3OH$).
Anal: Calcd. for $C_{16}H_{19}NO_5$(305.336): C,62.94; H,6.37; N,4.59. Found: C,63.02; H,6.15; N,4.48.

(b) With tetrabutyltin (S)-3-(Benzyloxycarbonyl)-4-(3-oxoheptyl)-5-oxazolidinone as an oil; $[\alpha]_D^{25}$ 67.9° (c 0.12, $CH_3OH$).
Anal: Calcd. for $C_{18}H_{23}NO_5$ EtOAc(421.494): C,62.69; H,7.41; N,3.32. Found: C,62.50; H,7.29; N,3.39.

Ten grams of the (S)-3-(benzyloxycarbonyl)-4-(3-oxobutyl)-5-oxazolidinone from Example 4 is dissolved in 480 ml of distilled tetrahydrofuran, followed by 160 ml of ammonia at 0° C. The reaction mixture is stirred at 0° for 5 hours, then at ambient temperature overnight. After stripping under vacuum to dryness, the reaction mixture yields a white solid which is recrystallized from hot ethyl acetate to give 8.8 g of (S)-2-(benzyloxycarbontlamino)-5-oxo-hexanamide as a white solid (82% yield), mp 142°–144°; $[\alpha]_D^{25} = -4.0°$ (c 0.4, $CH_3OH$).
Anal.: Calcd. for $C_7H_9NO_2$: C, 60.4; H, 6.4; N, 10.0. Found: C, 60.44; H, 6.53; N, 10.05.

By repeating the above procedure in a similar manner and substituting a stoichiometrically equivalent of the corresponding intermediates from the second previous paragraph, the following compounds are prepared:

(S)-2-Benzyloxycarbonylamino-5-oxo-heptanamide having a mp of 133°–135° C.;
$[\alpha]_D^{25}$ −4.17° (c 0.8, $CH_3OH$).
Anal: Calcd. for $C_{15}H_{20}N_2O_4$(292.341): C,61.63; H,6.90; N,9.58. Found: C,61.51; H,6.75; N,9.16.

(S)-2-Benzyloxycarbonylamino-5-oxo-nonamide having a mp of 162°–163° C.;
$[\alpha]_D^{25}$ −4.32° (c 0.6, $CH_3OH$).
Anal: Calcd. for $C_{17}H_{24}N_2O_4$(320.395): C,63.73; H,7.55; N,8.74. C,63.62; H,7.56; N,8.82.

To a solution of 2.8 g of (S)-2-benzyloxycarbonylamino)-5-oxohexanamide from the preceeding paragraph in a mixture of 60 ml of methanol and 7.5 ml of glacial acetic acid is added, under nitrogen, 1.5 g of palladium diacetate. This reaction mixture is hydrogenated under atmospheric pressure for 4 hrs, at which time a thin layer chromatographic analysis shows the reaction had gone to completion. The reaction mixture is then filtered through Celite and washed with methanol. The reaction mixture and washings are concentrated to dryness to give 1.7 g of a yellow oil, which is treated with 1 ml of a mixture of hydrochloric acid and ethyl acetate to produce the hydrochloride salt. This oil is triturated with methanol/ethyl ether to produce 1.3 g of a yellow solid; mp 174°–176° C.; $[\alpha]_D^{25} = -33°$ (c 0.96, $CH_3OH$). The yellow solid of (S)-cis-5-methylprolinamide (as the hydrochloride salt) is passed through a Bio-Rex 70 column (a weakly acid carboxylic acid ion-exchange resin) with elution first with 300-ml of water, followed by 1% solution of ammonium hydroxide. Concentration of the appropriate fractions gives a 0.9 g of a yellow solid, which is recrystallized from methylene chloride to produce 0.64 g of (S)-cis-S-methylprolinamide as a yellow solid (50% yield); mp 55°–56 °C.

By repeating the above procedure in a similar fashion, and substituting a stoichiometrically equivalent of the corresponding intermediate, the following compounds are prepared after reduction:
(S)-cis-5-ethylprolinamide, mp 63°-65° C.; and
(S)-cis-5-butylyprolinamide, mp 74°-75° C.

PREPARATION G 4.9 g of Boc-glycine was dissolved in a mixture of 50 ml. ethanol and 50 ml. distilled water. The pH of the solution was brought to 7 with aqueous cesium bicarbonate. The solvent was then removed under vacuum.

After 18 hours of drying under high vacuum, the residue was dissolved in 150 ml. dry DMF. 25 g chloromethylated polystyrene—1% divinylbenzene (Merrifield) resin (corresponding to 25 mmole chloride) was added. The mixture was shaken at 50° C. for 24 hours, filtered, and the resin was then washed sequentially with DMF, water, and ethanol. The resin was dried under vacuum for 3 days to yield 28.34 g of Boc-Gly-O-Resin.

EXAMPLE 1

In the reaction vessel of a Beckman 990 Peptide Synthesizer was placed 7.29 g. (5.5 mmol.) of Boc-Gly-O-Resin prepared by the reaction of equimolar ratios of the dry cesium salt of Boc-GlyOH with chloromethylpolystyrene/1% divinylbenzene. Amino acids were added sequentially to this resin by means of a synthesis program, as follows:

| Step | | | |
|---|---|---|---|
| 1 | $CH_2Cl_2$ wash | 1 time | 1.5 min |
| 2 | 50% $CF_3CO_2H/CH_2Cl_2$ - deprotection | 1 time | 1.5 min |
| 3 | 50% $CF_3CO_2H/CH_2Cl_2$ - deprotection | 1 time | 30 min |
| 4 | $CH_2Cl_2$ wash | 3 times | 1.5 min |
| 5 | 10% triethylamine/$CH_2Cl_2$ | 2 times | 1.5 min |
| 6 | $CH_2Cl_2$ wash | 3 times | 1.5 min |
| 7 | $N^\alpha$—Boc-amino acid solution | 1 time | add |
| 8 | N,N'—dicyclohexylcarbodiimide solution | 1 time | add |
| 9 | $CH_2Cl_2$ rinse and hold - coupling | 1 time | coupling reaction 2 hr |
| 10 | $CH_2Cl_2$ - rinse add | 1 time | 1.5 min |
| 11 | $CH_2Cl_2$ wash | 3 times | 1.5 min |
| 12 | ethanol wash | 3 times | 1.5 min |
| 13 | $CH_2Cl_2$ wash | 3 times | 1.5 min |

Steps 1-13 complete a coupling cycle for one amino acid and completeness of the reaction is checked by the ninhydrin method of E. Kaiser, et al., *Anal. Biochem.*, 34, 595 (1970).

The resin was coupled sequentially with a 2.0 to 2.5 molar excess of each protected amino acid and DCC. Thus, the resin was treated during successive coupling cycles with
3.01 g. Boc-Pro-OH,
5.99 g. Boc-Arg(Tosyl)-OH,
3.49 g. Boc-Leu-OH.$H_2O$ At this point, the resulting tetrapeptide resin was divided into smaller batches. A 1.00 g. batch was carried forward by further coupling in successive cycles with
0.456 g. Boc-D-Dia-OH toluenesulfonate,
0.44 g. Boc-Tyr(2,6-dichlorobenzyl)-OH,
0.375 g. Boc-Ser(Benzyl)-OH,
0.315 g. Boc-D-Nal(2)-OH,
0.35 g. Boc-D-p-F-Phe-OH,
0.275 g. Boc-L-Proline, and
2.5 ml. acetic anhydride.

The resin was removed from the reaction vessel, washed with $CH_2Cl_2$, and dried in vacuo to yield 1.66 g. of protected polypeptide resin. The protected peptide was removed from the resin by treatment at room temperature for 24 hours with 50 ml. of methanol saturated at 0° C. with ammonia. The resin beads were filtered and washed sequentially with methanol and DMF. Solvent was removed from the filtrate under vacuum to yield the protected peptide as 0.9 g. of yellow oil.

The protecting groups were removed by treatment with 10 ml. anhydrous liquid HF in the presence of 1 ml. of anisole (scavenger) in a Kel-F reaction vessel at 0° C. for 30 minutes. The HF was evaporated under vacuum and the residue of N-Ac-L-Pro-D-p-Cl-Phe-D-Nal(2)-Ser-Tyr-D-Dih-Leu-Arg-Pro-GlyNH₂, as its HF salt, was washed with ether. The residue was then extracted with glacial acetic acid. The acetic acid extract was lyophilized to yield 0.5 g. of crude material.

The crude material was converted to the acetate salt by passage in water through a column of AG3X (a weakly basic tertiary amine resin) which had been converted to the acetate form. Lyophilization of the eluate yielded 0.5 g. of the crude peptide acetate salt as a white solid.

The crude peptide was purified by high performance liquid chromatography on a 2.5×100 cm. column of Licroprep Rp-18 (25–40 micron) equilibrated to the running buffer 35% $CH_3$ CN/65%$H_2O$(0.03M in $NH_4$OAc, pH 4.5). The major UV absorbing (280 nm) peak eluting at approximately 3 column volumes was collected, concentrated to dryness, and lyophilized 3 times from distilled water to yield 75 mg of pure N-Ac-L-Pro-D-p-F-Phe-D-Nal(2)-Ser-Tyr-D-Dia-Leu-Arg-Pro-GlyNH₂, $[\alpha]_D^{25} = -15.4°$ (C 0.5, HOAc).

Proceeding in a similiar manner but substituting the appropriate A, B, C, D, E, G or F amino acid for those recited, there are prepared the corresponding GlyNH₂ decapeptides exemplified below.
N-Ac-L-Pro-D-p-F-Phe-D-Nal(2)-Ser-Tyr-D-Dih-Leu-Arg-Pro-GlyNH₂,
N-Ac-L-Pro-D-p-F-Phe-D-Nal(2)-Ser-Tyr-D-Iph-Leu-Arg-Pro-GlyNH₂,
N-Ac-D-Nal(2)-D-p-F-Phe-D-Nal(2)-Ser-Tyr-D-Iph-Leu-Arg-Pro-GlyNH₂,
N-Ac-D-p-Cl-Phe-D-p-Cl-Phe-D-Phe-Ser-Tyr-D-Iph-Leu-Arg-GlyNH₂,
N-Ac-L-Pro-D-p-F-Phe-D-Trp-Ser-Tyr-D-Dih-Leu-Arg-Pro-GlyNH₂,
N-Ac-L-Pro-D-p-F-Phe-D-Trp-Ser-Tyr-D-Dmh-Leu-Arg-Pro-GlyNH₂,
N-Ac-L-Pro-D-p-F-Phe-D-Trp-Ser-Tyr-D-Deh-Leu-Arg-Pro-GlyNH₂,
N-Ac-L-Pro-D-p-F-Phe-D-Trp-Ser-Tyr-D-Dph-Leu-Arg-Pro-GlyNH₂,
N-Ac-L-Pro-D-p-F-Phe-D-Trp-Ser-Tyr-D-Dhh-Leu-Arg-Pro-GlyNH₂,
N-Ac-L-Pro-D-p-F-Phe-D-Trp-Ser-Tyr-D-Prh-Leu-Arg-Pro-GlyNH₂,
N-Ac-L-Pro-D-p-F-Phe-D-Trp-Ser-Tyr-D-Hha-Leu-Arg-Pro-GlyNH₂,
N-Ac-L-Pro-D-p-F-Phe-D-Trp-Ser-Tyr-D-Dpa-Leu-Arg-Pro-GlyNH₂,
N-Ac-L-Pro-D-p-F-Phe-D-Trp-Ser-Tyr-D-Mpa-Leu-Arg-Pro-GlyNH₂,
N-Ac-L-Pro-D-p-F-Phe-D-Trp-Ser-Tyr-D-Pia-Leu-Arg-Pro-GlyNH₂, N-Ac-L-Pro-D-p-F-Phe-D-Trp-Ser-Tyr-D-Ppa-Leu-Arg-Pro-GlyNH$_2$,
N-Ac-L-Pro-D-p-F-Phe-D-Trp-Ser-Tyr-D-Bpa-Leu-Arg-Pro-GlyNH$_2$,
N-Ac-D-p-Cl-Phe-D-p-Cl-Phe-D-Trp-Ser-Tyr-D-Dmh-Leu-Arg-Pro-GlyNH$_2$,
N-Ac-D-p-Cl-Phe-D-p-Cl-Phe-D-Trp-Ser-Tyr-D-Deh-Leu-Arg-Pro-GlyNH$_2$,
N-Ac-D-p-Cl-Phe-D-p-Cl-Phe-D-Trp-Ser-Tyr-D-Dph-Leu-Arg-Pro-GlyNH$_2$,
N-Ac-D-p-Cl-Phe-D-p-Cl-Phe-D-Trp-Ser-Tyr-D-Dih-Leu-Arg-Pro-GlyNH$_2$,
N-Ac-D-p-Cl-Phe-D-p-Cl-Phe-D-Trp-Ser-Tyr-D-Dhh-Leu-Arg-Pro-GlyNH$_2$,
N-Ac-D-p-Cl-Phe-D-p-Cl-Phe-D-Trp-Ser-Tyr-D-Prh-Leu-Arg-Pro-GlyNH$_2$,
N-Ac-D-p-Cl-Phe-D-p-Cl-Phe-D-Trp-Ser-Tyr-D-Hha-Leu-Arg-Pro-GlyNH$_2$,
N-Ac-Nal(2)-D-p-F-Phe-D-Trp-Ser-Tyr-D-Dmh-Leu-Arg-Pro-GlyNH$_2$,
N-Ac-Nal(2)-D-p-F-Phe-D-Trp-Ser-Tyr-D-Deh-Leu-Arg-Pro-GlyNH$_2$,
N-Ac-Nal(2)-D-p-F-Phe-D-Trp-Ser-Tyr-D-Dph-Leu-Arg-Pro-GlyNH$_2$,
N-Ac-Nal(2)-D-p-F-Phe-D-Trp-Ser-Tyr-D-Dih-Leu-Arg-Pro-GlyNH$_2$,
N-Ac-Nal(2)-D-p-F-Phe-D-Trp-Ser-Tyr-D-Dhh-Leu-Arg-Pro-GlyNH$_2$,
N-Ac-Nal(2)-D-p-F-Phe-D-Nal(2)-Ser-Tyr-D-Dph-Leu-Arg-Pro-GlyNH$_2$,
N-Ac-Nal(2)-D-p-F-Phe-D-Trp-Ser-Tyr-D-Dhh-Leu-Arg-Pro-GlyNH$_2$,
N-Ac-Nal(2)-D-p-F-Phe-D-Trp-Ser-Tyr-D-Prh-Leu-Arg-Pro-GlyNH$_2$,
N-Ac-Nal(2)-D-p-F-Phe-D-Trp-Ser-Tyr-D-Hha-Leu-Arg-Pro-GlyNH$_2$,
N-Ac-Nal(2)-D-p-F-Phe-D-Trp-Ser-Tyr-PropylAmidine-Leu-Arg-Pro-GlyNH$_2$,
N-Ac-Nal(2)-D-p-F-Phe-D-Trp-Ser-Tyr-D-Mpa-Leu-Arg-Pro-GlyNH$_2$,
N-Ac-Nal(2)-D-p-F-Phe-D-Trp-Ser-Tyr-D-Pia-Leu-Arg-Pro-GlyNH$_2$,
N-Ac-Nal(2)-D-p-F-Phe-D-Trp-Ser-Tyr-D-Ppa-Leu-Arg-Pro-GlyNH$_2$,
N-Ac-Nal(2)-D-p-F-Phe-D-Trp-Ser-Tyr-D-Bpa-Leu-Arg-Pro-GlyNH$_2$,
N-Ac-Nal(2)-D-p-Cl-Phe-D-Trp-Ser-Tyr-D-Dph-Leu-Arg-Pro-GlyNH$_2$,
N-Ac-Nal(2)-D-p-Cl-Phe-D-Trp-Ser-Tyr-D-Dmh-Leu-Arg-Pro-GlyNH$_2$,
N-Ac-Nal(2)-D-p-Cl-Phe-D-Trp-Ser-Tyr-D-Deh-Leu-Arg-Pro-GlyNH$_2$, and
N-Ac-Nal(2)-D-p-Cl-Phe-D-Trp-Ser-Tyr-D-Dhh-Leu-Arg-Pro-GlyNH$_2$.

In a similar manner, by replacing the Boc-Gly-O-Resin with Boc-D-Ala-benzhydrylaminopolystyrene-1%-divinylbenzene resin prepared from benzhydrylaminopolystyrene-1% divinylbenzene resin (Beckman Inst), Boc-D-Ala-OH, DIC and HBT, was obtained the corresponding D-Ala$_{10}$ analogs of LHRH:
N-Ac-D-p-Cl-Phe-D-p-Cl-Phe-D-Nal(2)-Ser-Tyr-D-Iph-Leu-Arg-D-AlaNH$_2$, and
N-Ac-D-p-Cl-Phe-D-p-Cl-Phe-D-Trp-Ser-Tyr-D-Dih-Leu-Arg-Pro-D-AlaNH$_2$,
N-Ac-D-p-Cl-Phe-D-p-Cl-Phe-D-Trp-Ser-Tyr-D-Dmh-Leu-Arg-Pro-D-AlaNH$_2$,
N-Ac-D-p-Cl-Phe-D-p-Cl-Phe-D-Trp-Ser-Tyr-D-Deh-Leu-Arg-Pro-D-AlaNH$_2$,
N-Ac-D-p-Cl-Phe-D-p-Cl-Phe-D-Trp-Ser-Tyr-D-Dhh-Leu-Arg-Pro-D-AlaNH$_2$,
N-Ac-D-p-Cl-Phe-D-p-Cl-Phe-D-Trp-Ser-Tyr-D-Mpa-Leu-Arg-Pro-D-AlaNH$_2$,
N-Ac-D-p-Cl-Phe-D-p-Cl-Phe-D-Trp-Ser-Tyr-D-Pia-Leu-Arg-Pro-D-AlaNH$_2$,
N-Ac-D-p-Cl-Phe-D-p-Cl-Phe-D-Trp-Ser-Tyr-D-Ppa-Leu-Arg-Pro-D-AlaNH$_2$,
N-Ac-D-p-Cl-Phe-D-p-Cl-Phe-D-Trp-Ser-Tyr-D-Bpa-Leu-Arg-Pro-D-AlaNH$_2$,
N-Ac-D-Nal(2)-D-pCl-Phe-D-Trp-Ser-Tyr-D-Deh-Leu-Arg-Pro-D-AlaNH$_2$, $[\alpha]_D^{25} -21.6°$ (CO.4, HoAc),
N-Ac-D-Nal(2)-D-pCl-Phe-D-Trp-Ser-Tyr-D-Deh-Leu-Arg-Pro-D-AlaNH$_2$,
N-Ac-D-Nal(2)-D-pCl-Phe-D-Trp-Ser-Tyr-D-Dmh-Leu-Arg-Pro-D-AlaNH$_2$,
N-Ac-D-Nal(2)-D-pCl-Phe-D-Trp-Ser-Tyr-D-Dhi*-Leu-Arg-Pro-D-AlaNH$_2$,
N-Ac-D-Nal(2)-D-pCl-Phe-D-Trp-Ser-Tyr-D-Dph-Leu-Arg-Pro-D-AlaNH$_2$,
N-Ac-D-Nal(2)-D-pF-Phe-D-Trp-Dev-Tyr-D-Deh-Leu-Arg-Pro-D-AlaNH$_2$, and
N-Ac-D-Nal(2)-D-pF-Phe-D-Trp-Ser-Tyr-D-Dmh-Leu-Arg-Pro-D-AlaNH$_2$.

*D-Dhi is-D-N- epsilon dihydroimidazolinyllysine

EXAMPLE 2

For the synthesis of analogues with a C-terminal Pro-NHCH$_2$CH$_3$, a synthesis program identical to that described in Example 1 was used. The Beckman 990 Synthesizer reaction vessel was loaded with 2.13 g. of Boc-Pro-O-Resin, prepared by the reaction of equimolar ratios of the dry cesium salt of Boc-Pro-OH with chloromethyl-polystyrene/1% divinylbenzene (Lab Systems, Inc.). The quantity of Boc-Pro-O-Resin taken contained 1.4 mmol. of proline.

The resin was coupled sequentially with a 2.0 to 2.5 molar excess of each protected amino acid and DCC. Thus, the resin was reacted during successive coupling cycles with 1.61 g. Boc-Arg(Tosyl)-OH,
0.93 g. Boc-Leu-OH H$_2$O,
0.94 g. Boc-N,N'-guanido-diisopropylhomoarginine,
0.49 g. 1-hydroxybenzotriazole,
1.75 g. N-Boc-O-2-bromobenzyloxycarbonyl-L-tyrosine, and
1.11 g. Boc-Ser(Benzyl)-OH.

At this point in the synthesis the quantity of protected polypeptide resin was split in half and one half was carried through to completion by sequential reaction with 0.57 g. Boc-D-Nal(2)-OH,
0.480 g. Boc-D-p-F-Phe-OH
0.21 g. N-Ac-L-proline.

The resin was removed from the reaction vessel, washed with CH$_2$Cl$_2$, and dried in vacuo to yield 2.26 g. of protected polypeptide resin.

The protected polypeptide was cleaved from the resin by aminolysis with 25 mL. of ethylamine for 18 hours at 2° C. The ethylamine was allowed to evaporate and the resin was extracted with methanol. The methanol was evaporated to yield 1.39 g. of N-Ac-L-Pro-D-p-Cl-Phe-Trp-Ser(Benzyl)-Tyr(2,6-dichlorobenzyl)-D-Dih-Leu-Arg(Tosyl)-Pro-NHCH$_2$CH$_3$. This protected peptide was mixed with 3 ml of anisole and 30 mL. redistilled (from CoF$_3$) anhydrous liquid HF at 0° C. for 30 minutes in a Kel-F reaction vessel. The HF was evaporated under vacuum and the residue was washed with ether. The residue was dissolved in 2M acetic acid and lyophilized to yield 0.82 g. of crude N-Ac-L-Pro-D-p-F-Phe-Trp-Ser-Tyr-D-Dih-Leu-Arg-Pro-NHCH$_2$CH$_3$ as its acetic acid addition salt. Final purification was achieved by preparative high performance liquid chromatography of a 20 mg. sample on a 2.5×100 mm. column of 40-50 microns. octadecylsilylated silica (Merck, Lichroprep C$_{18}$).

Proceeding in a similiar manner, but substituting the appropriate protected amino acid residues where appropriate, there are prepared the following compounds:

N-Ac-D-Nal(2)-D-p-F-Phe-D-Trp-Ser-Tyr-D-Dih-Leu-Arg-Pro-NHEt,
N-Ac-D-Nal(2)-D-p-F-Phe-D-Trp-Ser-Tyr-D-Dph-Leu-Arg-Pro-NHEt,
N-Ac-D-Nal(2)-D-p-F-Phe-D-Trp-Ser-Tyr-D-Dmh-Leu-Arg-Pro-NHEt,
N-Ac-D-Nal(2)-D-p-F-Phe-D-Trp-Ser-Tyr-D-Deh-Leu-Arg-Pro-NHEt,
N-Ac-D-Nal(2)-D-p-F-Phe-D-Trp-Ser-Tyr-D-Dhh-Leu-Arg-Pro-NHEt,
N-Ac-D-Nal(2)-D-p-F-Phe-D-Trp-Ser-Tyr-D-Prh-Leu-Arg-Pro-NHEt,
N-Ac-D-Nal(2)-D-p-F-Phe-D-Trp-Ser-Tyr-D-Hha-Leu-Arg-Pro-NHEt,
N-Ac-D-Nal(2)-D-p-F-Phe-D-Trp-Ser-Tyr-D-Dpa-Leu-Arg-Pro-NHEt,

Repeating the above cleavage, substituting a stoichiometric amount of methylamine and propylamine for ethylamine there are obtained the corresponding methylamide or propylamine of the aforementioned nonapeptide.

EXAMPLE 3

Compounds of Formula I wherein H is —NH—CONH—R$^{10}$ may be prepared by classical solution synthesis.

For example, the following approach may be used wherein "AzaGlyNHR$_{10}$" is —NH—NH—CONH$_2$, to prepare the peptide as the free peptide or salt.

moval of the Cbz and nitro groups by hydrogenolysis, followed by coupling with N-Boc-N,N'-guanido-diethyl-D-homoarginine using DCC/HBT or other coupling agent known in the art. See Dutta, et al, supra, for a similar LHRH analogue synthesis.

Often, the fragments coupled in this way will be peptides or amino acids. Alternatively, the N-terminal nonapeptide acid may be prepared by the solid phase or solution method and subsequently coupled to semicarbazide-HCl by the dicyclohexylcarbodiimidehydroxybenzotriazole or other coupling method.

EXAMPLE 4

A. A solution of 0.1 g of the hydrogen fluoride salt of N-Ac-L-Pro-D-p-F-Phe-Trp-Ser-Tyr-D-Dia Leu-Arg-Pro-GlyNH$_2$ (See Example 1) is dissolved in 50 mL of water and passed through a column of 50 g Dowex 3 anion exchange resin which had previously been equilibrated with acetic acid and washed with deionized water. The column is eluted with deionized water and the effluent is lyophilized to yield the corresponding acetic acid salt of N-Ac-L-Pro-D-p-F-Phe-Trp-Ser-Tyr-D-Dia-Leu-Arg-Pro-Gly-NH$_2$, $[\alpha]_D^{25}-15.4°$ (C 1, HOAc).

Repeating the above, substituting other acids for acetic acid during the equilibration of the resin, there may be obtained, for example, the corresponding salts with hydrochloric acid, hydrobromic acid, sulfuric acid, phosphoric acid, nitric acid, benzoic acid, and the like.

Similarly there may be prepared the acid addition salts of the other peptides analogous to LHRH, described herein.

B. In the case of salts of low water solubility, these may be prepared by precipitation from water utilizing the desired acid. For example:

Zinc tannate salt—a solution of 10 mg of N-Ac-L-Pro-D-p-Cl-Phe-D-Nal(2)-Ser-Tyr-D-Dih-Leu-Arg-Pro-GlyNH$_2$ acetic acid salt in 0.1 mL of water was treated with a solution of 8 mg of tannic acid in 0.08 mL of 0.25M NaOH. A solution of 5 mg of ZnSO heptahy-

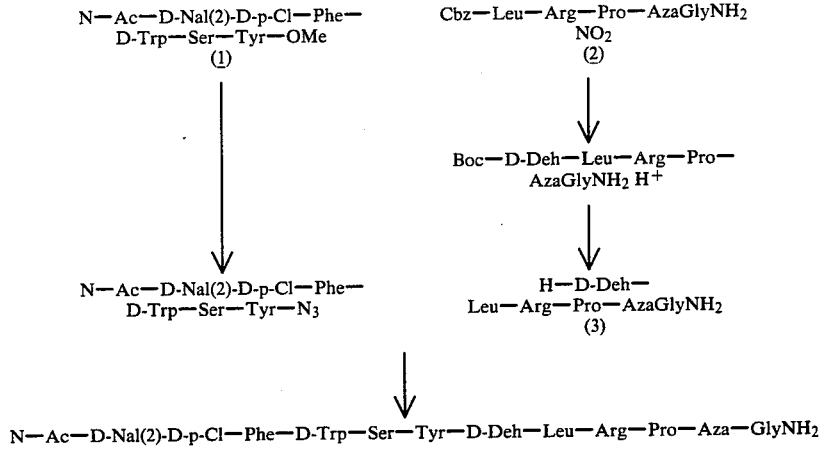

The coupling of the individual fragments may proceed by the acyl azide method (J. Honzel, et al, *Coll. Czech. Chem. Comm.*, 26, 2333 (1971), by DCC/HBT coupling or other racemization free fragment coupling techniques. Compound (2) is known: A. S. Dutta, et al., *J. Chem. Soc. Perkin I*, 1979, 379, and compound (1) may be prepared by methods analogous to those in Example 1. Compound (3) is prepared from (2) by redrate in 0.1 mL of water was immediately added to the solution of the LHRH analogue.

The resultant suspension was diluted with 1 mL water and the precipitate was centrifuged. The supernatant was decanted and the residue was washed twice with 1 mL portions of water by centrifugation of the precipitate and decantation of the supernatant. The precipitate was dried in vacuo to yield 15 mg of the mixed zinc tannate salt of the above named LHRH analogue.

Pamoate salt—to a solution of 50 mg N-Ac-L-Pro-D-p-F-Phe-D-Nal(2)-Ser-Tyr-D-Dih-Leu-Arg-Pro-Gly-NH$_2$ acetic acid salt in a mixture of 1.6 mL of ethanol and 0.1 mL of 0.25M NaOH was added solution of 11 mg of pamoic acid in 0.3 mL of 0.25M NaOH. The solvents were removed at reduced pressure and the residue was suspended in 2 mL of water, centrifuged, and the supernatant was decanted. The precipitate was washed with 1.5 mL H$_2$O, centrifuged, and the supernatant was decanted. The precipitate was dried in vacuo to yield 54 mg of the pamoate salt of the above named LHRH analogue.

In a similar manner other salts of low water solubility may be prepared.

C. Preparation of acid addition salt from free peptide.

To a solution of 50 mg of N-Ac-L-Pro-D-p-F-Phe-D-Nal(2)-Ser-Tyr-D-Dia-Leu-Arg-Pro-GlyNH$_2$ as the free base is added 30 mL of 1N acetic acid. The resulting solution is lyophilized to yield 50 mg. of the acetic acid salt of the above $[\alpha]_D^{25} - 15.4°$ (C 0.5, HOAc).

Similarly, replacing acetic acid with other acids (in stoichiometrically equivalent amounts relative to peptide) there was obtained other acid additon salts of the peptides herein, for example, the salts with hydrochloric acid, hydrobromic acid, sulfuric acid, phosphoric acid, nitric acid.

D. Preparation of salt with metal cation, e.g., zinc salt.

To a solution of 50 mg N-Ac-L-Pro-D-p-F-Phe-D-Nal(2)-Ser-Tyr-D-Dih-Leu-Arg-Pro-Gly-NH$_2$ acetic acid salt in a mixture of 0.4 mL of 0.25M NaOH, 0.3 mL water, and 1 mL ethanol was added a solution of 15 mg of ZnSO$_4$ heptahydrate in 0.2 ml of water. The precipitate was centrifuged and the supernatant was decanted. The precipitate was washed with 1 mL of water by centrifugation and decantation of the supernatant. The precipitate was dried in vacuo to yield the zinc salt of the above named LH-RH analogue.

In a similar manner salts with other multivalent cations e.g. calcium, bismuth, barium, magnesium, aluminum, copper, cobalt, nickel, cadmium and the like, may be prepared.

EXAMPLE 5

A solution of 50 mg of N-Ac-L-Pro-D-p-F-Phe-D-Nal(2)-Ser-Tyr-D-Dih-Leu-Arg-Pro-Gly-NH$_2$ acetic acid salt in 25 ml. of water is passed through a 50 g column of Dowex 1 (strongly basic, quaternary ammonium anion exchange resin) which had been equilibrated with NaOH solution to make the counter ion hydroxide. The column is eluted with 150 ml of water and the eluant is lyophilized to yield 45 mg of the corresponding polypeptide as the free base.

Similarly other acid addition salts of compounds of the peptides herein, e.g., those mentioned in Example 6, may be converted to the corresponding free bases.

EXAMPLE 6

The following are typical pharmaceutical compositions containing, as active ingredient, an LHRH antagonist of the present invention, for example N-Ac-L-Pro-D-p-F-Phe-D-Nal(2)-Ser-Tyr-D-Dih-Leu-Arg-Pro-GlyNH$_2$, by itself or as a pharmaceutically acceptable salt, e.g., the acetic acid addition salt, the zinc salt, the zinc tannate salt, etc.

| A. Tablet formulations for buccal (e.g. sublingual) administration: | |
|---|---|
| 1. LHRH Antagonist | 10.0 mg |
| Compressible Sugar, USP | 86.0 mg |
| Calcium Stearate | 4.0 mg |
| 2. LHRH Antagonist | 10.0 mg |
| Compressible Sugar, USP | 88.5 mg |
| Magnesium Stearate | 1.5 mg |
| 3. LHRH Antagonist | 5.0 mg |
| Mannitol, USP | 83.5 mg |
| Magnesium Stearate, USP | 1.5 mg |
| Pregelatinized Starch, USP | 10.0 mg |
| 4. LHRH Antagonist | 10.0 mg |
| Lactose, USP | 74.5 mg |
| Pregelatinized Starch, USP | 15.0 mg |
| Magnesium Stearate, USP | 1.5 mg |

Method of Manufacture a. LH-RH Antagonist is dissolved in water, a sufficient quantity to form a wet granulation when mixed with the sugar portion of the excipients. After complete mixing, the granulation is dried in a tray or fluid-bed dryer. The dry granulation is then screened to break up any large aggregates and then mixed with the remaining components. The granulation is then compressed on a standard tabletting machine to the specific tablet weight.

b. In this manufacturing method, all formulations would include 0.01% gelatin, USP. The gelatin would be first dissolved in the aqueous granulation solvent followed by the LH-RH analog. The remaining steps are as in (a) above.

Formulation 4 could also be used as a tablet for oral administration.

| B. Long Acting intramuscular injectable formulation. | |
|---|---|
| 1. Long Acting I.M. Injectable - Sesame Oil Gel | |
| LHRH Antagonist | 10.0 mg |
| Aluminum monostearate, USP | 20.0 mg |
| Sesame oil q.s. ad | 1.0 ml |

The aluminum monostearate is combined with the sesame oil and heated to 125° C. with stirring until a clear yellow solution forms. This mixture is then autoclaved for sterility and allowed to cool. The LH-RH analogue is then added aseptically with trituration. Particularly preferred LH-RH analogues are salts of low solubility, e.g. zinc salts, zinc tannate salts, pamoate salts, and the like. These exhibit exceptionally long duration of activity.

| 2. Long Acting I.M. Injectable - Biodegradable Polymer Microcapsules | |
|---|---|
| LHRH Antagonist | 1% |
| 25/75 glycolide/lactide copolymer (0.5 intrinsic viscosity) | 99% |
| Microcapsules (0–150*) of above formulation suspended in: | |
| Dextrose | 5.0% |
| CMC, sodium | 0.5% |
| Benzyl alcohol | 0.9% |
| Tween 80 | 0.1% |
| Water, purified q.s. | 100.0% |

25 mg of microcaspsules would be suspended in 1.0 ml of vehicle.

| C. Aqueous Solution for Intramuscular Injection | |
|---|---|
| LHRH Antagonist | 500 mg |
| Gelatin, nonantigenic | 5 mg |
| Water for injection q.s. ad | 100 ml |

Dissolve gelatin and LHRH antagonist in water for injection, then sterile filter solution.

| D. Formulation for Rectal Administration | |
|---|---|
| Suppository Vehicle for Rectal Administration | |
| LHRH Antagonist | 5.0 mg |
| Witepsol H15 | 20.0 gm |

The LHRH antagonist is combined with the molten Witepsol H15, mixed well and poured into 2 gm molds.

EXAMPLE 7

Biological Activity

The useful activity of the compounds of the invention is illustrated by the following results obtained in the standard anti-ovulation test of A. Corbin and C. W. Beattie, Endocr. Res. Commun. Vol. 2, page 1, 1975.

| Compound Structure | | | | | ED$_{50}$ in μgs | |
|---|---|---|---|---|---|---|
| | | | | | Propylene Glycol/saline | Corn Oil |
| 1 | 2 | 3 | 6 | 10 | noon–24 hrs | noon–24 hrs |
| N-Ac-D-pClPhe, | D-pClPhe, | D-Trp, | D-Dph, | D-Ala | 2.6 | −2.0 | 14 |
| N-Ac D-Nal(2), | D-pFPhe, | D-Trp, | D-Dph, | — | 2.4 | −4.7 | 12 |
| N-Ac D-Nal(2), | D-pFPhe, | D-Trp, | D-Deh, | — | 1.6 | 1.4 | 3.5 |
| N-Ac-D-p-Cl-Phe, | D-p-Cl-Phe, | D-Trp,- | D-Deh, | — | 2.0 | 2.4 | 16 |
| N-Ac-D-p-ClPhe, | D-p-ClPhe, | D-Trp, | D-Dph, | — | 2.6 | 2.3 | |
| N-Ac-D-p-Cl-Phe, | D-p-Cl-Phe, | D-Trp, | D-Deh, | D-Ala$^{10}$ | 1.7 | 1.6 | >8 |
| N-Ac-D-p-Cl-Phe, | D-p-Cl-Phe, | D-Trp, | D-Dmh, | D-Ala$^{10}$ | 1.6 | 1.3 | 1.8 |
| N-Ac-D-p-Cl-Phe, | D-p-Cl-Phe, | D-Trp, | D-Dhi, | D-Ala$^{10}$ | 2.0 | 2.0 | 3.6 |
| N-Ac-D-Nal(2), | D-p-F-Phe, | D-Trp, | D-Dmh, | — | 1.7 | 0.8 | 3.3 |
| N-Ac-D-Nal(2), | D-p-F-Phe, | D-Trp, | D-Dhi, | — | 1.7 | 1.0 | 2.8 |
| N-Ac-D-Nal(2), | D-p-Cl-Phe, | D-Trp, | D-Deh, | — | 2.0 | 1.0 | 1.7 |
| N-Ac-D-Nal(2), | D-p-Cl-Phe, | D-Trp, | D-Deh, | D-Ala$^{10}$ | 0.67 | 0.5 | 2.5 |

EXAMPLE 8

Characterizing data for compounds prepared according to the previous Examples is shown below:

| Cpd # | Compound |
|---|---|
| 1 | [N—Ac—D-pCl-Phe$^{1,2}$,D-Trp$^3$,D-Dih$^6$,D-Ala$^{10}$]LHRH (second peak) |
| 2 | [N—Ac—Pro$^1$,D-pF-Phe$^2$,D-Nal(2)$^3$, D-monoisopropylArg$^6$]LHRH |
| 3 | [N—Ac—Pro$^1$,D-pF-Phe$^2$,D-Nal(2)$^3$,D-Dia$^6$]LHRH |
| 4 | [N—Ac—Pro$^1$,D-pF-Phe$^2$,D-Nal(2)$^3$, D-monoisopropylArg$^6$,Pro$^9$-NHEt]LHRH |
| 5 | [N—Ac—Pro$^1$,D-pF-Phe$^2$,D-Nal(2)$^3$,D-Dia$^6$, Pro$^9$—NHE]LHRH |
| 6 | [N—Ac—D-Nal(2)$^{1,3}$,D-pF-Phe$^2$,D-Dph$^6$]LHRH |
| 7 | [N—Ac—Pro$^1$,D-pF-Phe$^2$,D-Nal(2)$^3$,D-Dph$^6$]LHRH |
| 8 | [N—Ac—D-pCl-Phe$^{1,2}$,D-Trp$^3$,D-Dph$^6$,D-Ala$^{10}$]LHRH |
| 9 | [N—Ac—D-pCl-Phe$^{1,2}$,D-Trp$^3$,D-Dph$^6$]LHRH |
| 10 | [N—Ac—D-Nal(2)$^1$,D-pF-Phe$^2$,D-Trp$^3$,D-Dph$^6$]LHRH (second peak) |
| 11 | [N—Ac—D-Nal(2)$^1$,D-pF-Phe$^2$,D-Trp$^3$,D-Dph$^6$]LHRH (third peak) |
| 12 | [N—Ac—D-pCl-Phe$^{1,2}$,D-Trp$^3$,D-Dhh$^6$D-Ala$^{10}$]LHRH |
| 13 | [N—Ac—D-Ser$^1$-D-pF-Phe$^2$,D-Trp$^3$,D-Dhh$^6$]LHRH |
| 14 | [N—Ac—D-Nal(2)$^1$-D-pF-Phe$^2$,D-Trp$^3$,D-Dhh$^6$]LHRH |
| 15 | [N—Ac—D-pCl-Phe$^{1,2}$,D-Trp$^3$,D-Deh$^6$]LHRH |
| 16 | [N—Ac—D-Nal(2)$^1$,D-pF-Phe$^2$,D-Trp$^3$,D-Deh$^6$]LHRH |
| 17 | [N—Ac—D-pCl-Phe$^{1,2}$,D-Trp$^3$,D-Deh$^6$D-Ala$^{10}$]LHRH |
| 18 | [N—Ac—D-Nal(2)$^1$D-pCl—Phe$^2$,D-Trp$^3$,D-Deh$^6$D]-LHRH |
| 19 | [N—Ac—D-Nal(2)$^1$,D-pCl-Phe$^2$,D-Trp$^3$,D-Deh$^6$D-Ala$^{10}$]LHRH |
| 20 | [N—Ac—D-pCl-Phe$^{1,2}$,D-Trp$^3$,D-Wsh$^6$]LHRH |
| 21 | [N—Ac—D-Nal(2)$^1$,D-pF-Phe$^2$,D-Trp$^3$,D-Wsh$^6$]LHRH |
| 22 | [N—Ac—D-pCl-Phe$^{1,2}$,D-Trp$^3$,D-Dmh$^6$,D-Ala$^{10}$]LHRH |
| 23 | [N—Ac—D-Nal(2)$^1$,D-pF-Phe$^2$,D-Trp$^3$,D-Dmh$^6$]LHRH |
| 24 | [N—Ac—D-pCl-PheDhu 1,2,D-Trp$^3$,D-Dhi$^6$D-Ala$^{10}$]LHRH |
| 25 | [N—Ac—D-Nal(2)$^1$-D-pF-Phe$^2$,D-Trp$^3$,D-Dhi$^6$D]LHRH |
| 26 | [N—Ac—D-pCl-Phe$^{1,2}$,D-Trp$^3$,D-Dma$^6$D,D-Ala$^{10}$]-LHRH[N$^G$,N$^{G1}$—dimethyl arginine: Dma; N$^G$—ehtyl,N$^{G1}$—dimethylaminopropylhomoarginine: Wsh] |

Physical Data 1. mp 157–160°. See Note 2. Amino acid analysis (909): Ser, 0.82 (1); Pro, 1.12 (1); Ala, 1.14 (1); Leu, 1.16 (1); Tyr, 0.83 (1); NH$_3$, 2.58; Arg, 0.88 (1); D-pCl-Phe + Trp, 2.34 (3); D-Dih, 1.15 (1).

2. mp 144–150°; [α]$_D^{25}$ −24.0° (c 0.3, HOAc). Calcd. for C$_{73}$H$_{104}$N$_{17}$F (1510.75): C, 58.04; H, 6.94; N, 15.76. Found (143316): C, H low. Amino acid analysis (924): Ser, 0.87 (1); Pro, 2.08 (2); Gly, 1.01 (1); mono-isopropyl Arg, 0.85 (1); Leu, 1.02 (1); Tyr, 0.90 (1); NH$_3$, 1.33 (1); Arg, 1.06 (1); D-pF-Phe, 0.91 (1); D-Nal(2), 1.09 (1).

3. mp 144–148°; [α]$^{25}_D$ −15.4° (c 0.32, HOAc). Calcd. for C$_{76}$H$_{110}$N$_{17}$O$_{17}$F (1552.83): C, 58.78; H, 7.14; N, 15.33. Found (144251): C, H low. Amino acid analysis (923): Ser, 0.94 (1); Pro, 2.05 (2); Gly, 1.00 (1); D-Dia, 0.85 (1); Leu, 1.03 (1); Tyr, 0.96 (1); NH$_3$, 1.27 (1); Arg, 1.01 (1); D-pF-Phe, 0.95 (1); D-Nal(2), 1.06 (1).

4. mp 145–150°; [α]$_D^{25}$ −18.1° (c 0.83, HOAc). See Note 2. Amino acid analysis (925): Ser, 0.91 (1); Pro, 2.09 (2); Leu, 1.05 (1); Tyr, 0.84 (1); NH$_3$, 0.41; Arg, 1.11 (1); D-pF-Phe, 0.91 (1); D-Nal(2), 0.95 (1); mono-isopropyl Arg, 0.74 (1).

5. mp 137–142°; [α]$_D^{25}$ −16.5° (c 0.2, HOAc). Calcd. for C$_{76}$H$_{111}$N$_{16}$O$_{16}$F (1523.83): C, 59.90; H, 7.34; N, 14.71. Found (143315): C, H low. Amino acid analysis (926): Ser, 0.91 (1); Pro, 2.25 (2); Leu, 1.05 (1); Tyr, 0.93 (1); NH$_3$, 0.67; Arg, 1.01 (1); D-pF-Phe, 1.00 (1); D-Nal(2), 1.05 (1); D-Dia, 0.86 (1).

6. mp 152–155°; [α]$_D^{25}$ −15.2° (c 0.2, HOAc). Calcd. for C$_{85}$H$_{116}$N$_{17}$O$_{17}$F (1667): C, 61,24; H, 7.01; N, 14.28. Found (143304): C, H low. Amino acid analysis (939): Ser, 0.94 (1); Pro, 1.11 (1); Gly, 1.02 (1); Leu, 1.02 (1); Tyr, 0.90 (1); NH$_3$, 1.45 (1); Arg, 1.06 (1); D-pF-Phe, 0.94 (1); D-Dph, 1.06 (1); D-Nal(2), 2.32 (2).

7. mp 135–142°; [α]$_D^{25}$ −26.5° (c 0.23, HOAc). Calcd. for C$_{77}$H$_{112}$N$_{17}$O$_{17}$F (1566.26): C, 59.02; H, 7.20; N, 15.20. Found (143303): C, H low. Amino acid analysis (940): Ser, 0.88 (1); Pro, 2.02 (2); Gly, 1.03 (1); Leu, 1.00 (1); Tyr, 0.88 (1); NH$_3$,

| Cpd # | Compound |
|---|---|
| | 1.61; Arg, 1.08 (1); D-pF-Phe, 0.92 (1); D-Dph, 1.08 (1); D-Nal(2), 0.91 (1). |
| 8. | mp 170–172°; $[\alpha]_D^{25}$ −17.5° (c 0.37, HOAc). Calcd. for $C_{80}H_{114}N_{18}O_{17}O_{17}Cl_2$ (1670.82): C, 57.51; H, 6.88; N, 15.09. Found (143294): C, H low. Amino acid analysis (945): Ser, 0.88 (1); Pro, 1.09 (1); Ala, 0.88 (1); Leu, 1.01 (1); Tyr, 0.92 (1); $NH_3$, 1.76; Trp, 0.41 (1); Arg, 1.19 (1); D-pCl—Phe, 1.84 (2); D-Dph, 0.97 (1). Note: Trp does not separate well from D-pCl-Phe.) |
| 9. | mp 165–170°; $[\alpha]_D^{25}$ −25° (c 0.43, HOAc). Calcd. for $C_{79}H_{112}N_{18}O_{17}Cl_2$ (1656.2): C, 57.27; H, 6.81; N, 15.22. Found (142675): C, H low. Amino acid analysis (981): Ser, 0.83 (1); Pro, 0.93 (1); Ala, 1.01 (1); Leu, 1.02 (1); Tyr, 0.94 (1); $NH_3$, 1.18 (1); Trp, 0.97 (1)[1]; Arg, 1.03 (1); D-pCl—Phe, 1.94 (2)[1]; D-Dph, 1.16 (1). |
| 10. | mp 142–150°; $[\alpha]_D^{25}$ solution opaque in HOAc. Calcd. for $C_{82}H_{113}N_{18}O_{17}F$ (1641.93): C, 59.98; H, 6.94; N, 15.35. Found (143302): C, H low. Amino acid analysis (953B): Ser, 0.95 (1); Pro, 0.93 (1); Gly, 1.10 (1); Leu, 1.09 (1); Tyr, 0.87 (1); D-pF-Phe, 0.223 (1); $NH_3$, 2.87; Trp, 0.413 (1); Arg, 0.94 (1); D-Dph, 1.25 (1); D-Nal(2), 1.06 (1). (Note: D-pF-Phe values are low.) |
| 11. | mp 142–152°. See note 2. Amino acid analysis (952): Ser, 0.83 (1); Pro, 0.95 (1); Gly, 0.97 (1); Leu, 1.06 (1); Tyr, 0.96 (1); $NH_3$, 3.17; Trp, 0.66 (1); Arg, 1.01 (1); D-pF-Phe, 0.78 (1); D-Dph, 1.22 (1); D-Nal(2), 1.27 (1). |
| 12. | mp 140–142°; $[\alpha]_D^{25}$ −14.3° (c 0.14, HOAc). Calcd. for $C_{82}H_{118}N_{18}O_{13}Cl_2 \cdot 4\ CH_3COOH \cdot 3\ H_2O$ (1929.14): C, 56.03; H, 7.31; N, 13.07. Found (141592): C, 55.75; H, 6.93; N, 12.76. Amino acid analysis (987): Ser, 0.87 (1); Pro, 1.09 (1); Ala, 1.08 (1); Leu, 1.02 (1); Tyr, 0.94 (1); $NH_3$, 1.43; Trp, 0.88 (1)[1]; Arg, 0.97 (1); D-pCl—Phe, 1.76 (2)[1]; D-Dhh does not come off column even after 340 min. |
| 13. | mp 145–148°; $[\alpha]_D^{25}$ −4.17° (c 0.11, HOAc). Calcd. for $C_{79}H_{121}N_{18}O_{18}F$ (1629.96): C, 58.21; H, 7.48; N, 15.46. Found (142506): C, H low. Amino acid analysis (963B): Ser, 1.77 (2); Pro, 1.15 (1); Gly, 1.07 (1); Leu, 1.01 (1); Tyr, 0.96 (1); $NH_3$, 1.26; Trp, 0.73 (1); Arg, 1.01; D-pF-Phe, 0.81 (1). |
| 14. | mp 147–151°; $[\alpha]_D^{25}$ −27.3° (c 0.51, HOAc). Calcd. for $C_{89}H_{127}N_{18}O_{17}F$ (1740.12): C, 61,43; H, 7.36; N, 14.49. Found (142505): C, H low. Amino acid analysis (964B): Ser, 1.00 (1); Pro, 1.11 (1); Gly, 1.03 (1); Leu, 1.03 (1); Tyr, 0.95 (1); $NH_3$, 1.24 (1); Trp, 0.80 (1); Arg, 0.99 (1); D-pF-Phe, 0.87 (1); D-Nal(2), 0.85 (1). |
| 15. | mp 155–158°; $[\alpha]_D^{25}$ −26° (c 0.44, HOAc). Calcd. for $C_{77}H_{108}N_{18}O_{17}Cl_2$ (1628.74): C, 56.78; H, 6.68; N, 15.48. Found (142479): C, H low. Amino acid analysis (975): Ser, 0.88 (1); Pro, 0.97 (1); Gly, 1.01 (1); Leu, 0.99 (1); Tyr, 0.97 (1); $NH_3$, 1.19; Trp, 0.926 (1)[1]; Arg, 1.03 (1); D-pCl—Phe, 1.85 (2)[1]; D-Deh, 1.28 (1). |
| 16. | mp 152–155°; $[\alpha]_D^{25}$ −32.6° (c 0.26, HOAc). Calcd. for $C_{81}H_{111}N_{18}O_{17}F$ (1628): C, 59.76; H, 6.87; N, 15.49. Found (142481): C, H low. Amino acid analysis (966): Ser, 0.93 (1); Pro, 0.99 (1); Gly, 1.10 (1); Leu, 0.94 (1); Tyr, 0.94 (1); $NH_3$, 1.19; Trp, 0.76 (1); Arg, 1.02 (1); D-pF-Phe, 0.92 (1); D-Deh, 1.23 (1); D-Nal(2), 0.95 (1). |
| 17. | mp 155–157°; $[\alpha]_D^{25}$ −18.4° (c 0.27, HOAc). Calcd. for $C_{78}H_{110}N_{18}O_{17}O_{17}\ Cl_2$ (1642.76): C, 57.03; H, 6.75; N, 15.35. Found (143293): C, H low. Amino acid analysis (997): Ser, 0.89 (1); Pro, 0.97 (1); Ala, 0.98 (1); Leu, 1.03 (1); Tyr, 0.99 (1); $NH_3$, 1.34; Trp, 0.93 (1)[1]; Arg, 1.00 (1); D-pCl—Phe, 1.86 (2)[1]; D-Deh, 1.17 (1). |
| 18. | mp 158–160°; $[\alpha]_D^{25}$ −29.3°(c 0.41, HOAc). Calcd. for $C_{81}H_{111}N_{18}O_{17}Cl$ (1644.36): C, 59.16; H, 6.80; N, 15.33. Found (143809): C, H low. Amino acid analysis (1014): Ser, 0.92 (1); Pro, 1.02 (1); Gly, 1.02 (1); Leu, 1.02 (1); Tyr, 0.99 (1); $NH_3$, 1.26; Trp, 0.83 (1); Arg, 0.98 (1); D-pCl—Phe, 0.98 (1); D-Deh, 1.16 (1); D-Nal(2), 0.96 (1). |
| 19. | mp 154–157°; $[\alpha]_D^{25}$ −21.6° (c 0.25, HOAc). Calcd. for $C_{82}H_{113}N_{18}O_{17}Cl$ (1658.38): C, 58.39; H, 6.87; N, 15.20. Found (144272): C, H low. Amino acid analysis (1022): Ser, 0.95 (1); Pro, 1.08 (1); Ala, 0.99 (1); Leu, 1.02 (1); Tyr, 1.01 (1); $NH_3$, 1.34; Trp, 0.85 (1); Arg, 0.97 (1); D-pCl—Phe, 1.18 (1); D-Deh,[*] 1.17 (1); D-Nal(2), 1.00 (1). |
| 20. | mp 150–155°; $[\alpha]_D^{25}$ −17.9° (c 0.25, HOAc). Calcd. for $C_{80}H_{115}N_{19}O_{17}Cl_2$ (1685.84): C, 56.99; H, 6.87; N, 15.79. Found (143292): C, H low. Amino acid analysis (995): Ser, 0.86 (1); Pro, 1.08 (1); Gly, 1.04 (1); Leu, 0.97 (1); Tyr, 0.91 (1); $NH_3$, 1.32; Trp, 0.31 (1); Arg, 0.99 (1); D-pCl—Phe, 1.34 (2); D-Wsh does not come off column even after 340 min. |
| 21. | mp 150–154°; $[\alpha]_D^{25}$ −28.3°(c 0.55, HOAc). Calcd. for $C_{84}H_{118}N_{19}O_{17}F$ (1685): C, 59.88; H, 7.06; N, 15.79. Found (143295): C, H low. Amino acid analysis (996): Ser, 0.87 (1); Pro, 0.94 (1); Gly, 1.05 (1); Leu, 0.99 (1); Tyr, 0.95 (1); D-pF-Phe, 0.90 (1); $NH_3$, 1.34; Trp, 0.68 (1); Arg, 1.00 (1); D-Nal(2), 0.846 (1); D-Wsh does not come off column even after 340 minutes. |
| 22. | mp 164–166°; $[\alpha]_D^{25}$ −12.7° (c 0.3, HOAc). Calcd. for $C_{76}H_{106}N_{18}O_{17}Cl_2$ (1614.72): C, 56.53; H, 6.62; N, 15.61. Found (143660): C, H low. Amino acid analysis (1011): Ser, 0.93 (1); Pro, 1.07 (1); Ala, 1.03 (1); Leu, 1.00 (1); Tyr, 0.97 (1); $NH_3$, 1.27; Trp, 0.95 (1)[1]; Arg, 1.11 (1); D-pCl—Phe, 1.9 (2)[1]; D-Dmh, 1.11 (1). |
| 23. | mp 160–164°; $[\alpha]_D^{25}$ −26.5° (c 0.29, HOAc). Calcd. for $C_{79}H_{107}N_{18}O_{17}F$ (1600): C, 59.31; H, 6.74; H, 6.74; N, 15.76. Found (143658): C, H low. Amino acid analysis (1012): Ser, 0.87 (1); Pro, 1.06 (1); Gly, 1.00 (1); Leu, 1.02 (1); Tyr, 0.98 (1); $NH_3$, 1.31; Trp, 0.87 (1); Arg, 1.08 (1)1; D-pF-Phe, 1.25 (1); D-Dmh 1.08[1]; D-Nal(2), 0.89 (1). |
| 24. | mp 160–165°; $[\alpha]_D^{25}$ −12.2° (c 0.29, HOAc). Calcd. for $C_{76}H_{104}N_{18}O_{17}Cl_2$ (1612.7): C, 56.60; H, 6.50; N, 15.60. Found (143659): C, H low. Amino acid analysis (1010): Ser, 0.94 (1); Pro, 1.14 (1); Ala, 1.01 (1); Leu, 0.97 (1); Tyr, 0.96 (1); $NH_3$, 1.23; Trp, 1.00[1]; Arg, 1.06 (1); D-pCl—Phe, 2.00 (2)[1]; D-Dhi, 0.99 (1). |
| 25. | mp 172–174°; $[\alpha]_D^{25}$ −29.8° (c 0.62, HOAc). Calcd. for $C^{79}H_{105}N_{18}O_{17}F$ (1598): C, 59,38; H, 6.62; N, 15.78. Found (143657): C, H low. Amino acid analysis (1013): Ser, 0.89 (1); Pro, 1.07 (1); Gly, 1.00 (1); Leu, 0.99 (1); Tyr, 0.97 (1); $NH_3$, 1.24 (1); Trp, 0.85 (1); Arg, 1.04 (1); D-pF-Phe, 0.98 (2); D-Nal(2), 0.92 (1); D-Dhi, 0.98 (1). |
| 26. | mp 162–164°; $[\alpha]$ −18.7° (c 0.54, HOAc). $D^{25}$ Calcd. for $C_{75}H_{104}N_{18}O_{17}Cl_2$ (1600.69): C, 56.28; H, 6.55; N, 15.75. Found (143808): C, H low. Amino acid analysis (1015): Ser, 0.86 (1); Pro, 1.14 (1); Ala, 1.01 (1); Leu, 1.01 (1); Tyr, 0.99 (1); $NH_3$, 1.54; Trp, 1.02 (1)[1]; Arg, 0.99 (1); D-pCl—Phe, 2.04 (2)[1]; D-Dma, 1.02 (1)[1]. |

NOTES
[1]Peaks do not separate well, and values assigned are the average for the two peaks.
[2]Optical rotation and elemental analysis were not carried out due to lack of sufficient material.

Also prepared were:
N—Ac—D-Nal(2)—D-p-Cl—Phe—D-Nal(2)—Ser—Tyr—D-Deh—Leu—Arg—Pro—D-AlaNH₂;
N—Ac—D-Nal(2)—D-p-F—Phe—D-Nal(2)—Ser—Tyr—D-Deh—Leu—Arg—
N—Ac—D-Trp—D-p-Cl—Phe—D-Nal(2)—Ser—Tyr—D-Deh—Leu—Arg—Pro—D-AlaNH₂;
N—Ac—D-Trp—D-p-Cl—Phe—Phe—D-Trp—Ser—Tyr—D-Deh—Leu—Arg—Pro—D-AlaNH₂.

What is claimed is:
1. A compound of formula

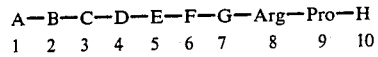 (I)

and the pharmaceutically acceptable salts thereof, wherein:

A is an amino acyl residue selected from the group consisting of L-pyroglutamyl, D-pyroglutamyl, N-acyl-D,L-tryptophanyl, N-acyl-glycyl, N-Ac-D,,L-$\Delta^{3,4}$-prolyl, N-Ac-D,L-prolyl, N-Ac-L-alkylprolyl, N-Ac-D,L-phenylalanyl, N-Ac-D,L-p-chlorophenylalanyl, N-Ac-D,L-seryl, N-Ac-D,L-threonyl, N-Ac-D,L-alanyl, 3-(1-naphthyl)-D,L-alanyl, 3-(2-naphthyl)-D,L-alanyl, 3-(2,4,6-trimethylphenyl)-D,L-alanyl, 3-(4-trifluoromethylphenyl)-D,L-alanyl, 3-(9-anthryl)-D,L-alanyl, 3-(2-fluorenyl)-D,L-alanyl, and 3-(Het)-D,L-alanyl wherein Het is a heterocyclic aryl containing radical selected from

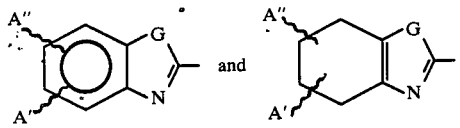

wherein A″ and A′ are independently selected from the group consisting of hydrogen, lower alkyl, chlorine and bromine, and G is selected from the group consisting of oxygen, nitrogen and sulfur;

B is an amino acyl residue selected from the group consisting of D-phenylalanyl, D-p-Cl-phenylalanyl, D-p-F-phenylalanyl, D-p-nitrophenylalanyl, 3-(3,4,5-trimethoxyphenyl)-D-alanyl, 2,2-diphenylglycine, D-α-methyl-p-Cl-phenylalanine and 3-(2,4,6-trimethylphenyl)-D-alanyl;

C is an amino acyl residue selected from the group consisting of L-tryptophanyl, D-tryptophanyl, D-phenylalanyl, D-Me₅phenylalanyl, 3-(2-pyridyl)-D-alanyl, 3-(3-pyridyl)-D-alanyl, 3-(4-pyridyl)-D-alanyl, 3-(1-naphthyl)-D-alanyl, and 3-(2-naphthyl)-D-alanyl;

D is an amino acyl residue selected from the group consisting of L-seryl, and D-alanyl;

E is an amino acyl residue selected from the group sisting of L-phenylalanyl and L-tyrosyl;

F is an amino acyl selected from the group consisting of the radicals represented by the following structural formulas:

(a)

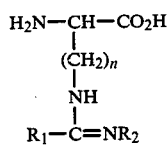 (II)

wherein
n is 1 to 5;
$R_1$ is alkyl of 1 to 12 carbon atoms, —NRR₃ wherein R is hydrogen or alkyl of 1 to 4 carbon atoms, $R_3$ is alkyl of 1 to 12 carbon atoms, cycloalkyl, phenyl, benzyl, —(CH₂)n-morpholino or —(CH₂)ₙN(R₄)₂ wherein n is 1 to 5 and $R_4$ is lower alkyl;

$R_2$ is hydrogen or $R_3$; or $R_1$ and $R_2$ comprise a ring represented by the following structural formulas:

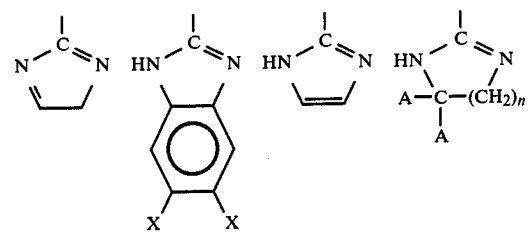

wherein n is 1 to 7; A is hydrogen, alkyl of 1 to 6 carbon atoms or cycloalkyl; and X is halo or A or (b)

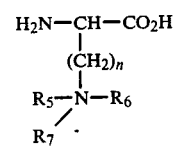 (III)

wherein $R_5$ is alkyl of 1 to 6 carbon atoms, benzyl, phenylethyl, cyclohexyl, cyclopentyl; and $R_6$ and $R_7$ are hydrogen or alkyl of 1 to 4 carbon atoms; and n is the integer 2–5; or (c) a substituent of the formula

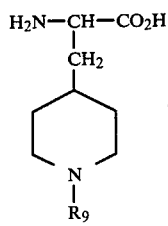 (IV)   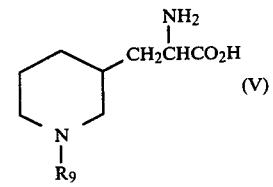 (V)

wherein $R_9$ is hydrogen, alkyl of 1 to 12 carbon atoms, phenyl or phenylloweralkyl;

G is an amino acyl residue selected from the group consisting of L-leucyl, L-norleucyl and L-norvalyl;

H is D-alaninamide, D-leucinamide, glycinamide or —NHR₅ wherein $R_5$ is lower alkyl, cycloalkyl, fluoro lower alkyl, or NHCONH—R₁₀ wherein $R_{10}$ is hydrogen or lower alkyl; and the pharmaceutically acceptable salts thereof.

2. A compound according to claim 1 of the formula

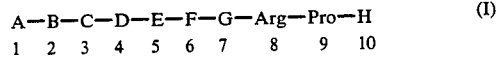 (I)

and the pharmaceutically acceptable salts thereof, wherein:

A is an amino acyl residue selected from the group consisting of N-Ac-D,L-$\Delta^{3,4}$-prolyl, N-Ac-D,L-prolyl, N-Ac-L-alkylprolyl, N-Ac-D,L-phenylalanyl, N-Ac-D,L-p-chlorophenylalanyl, N-Ac-D,L-seryl, N-Ac-D,L-threonyl, N-Ac-D,L-alanyl, 3-(1-naphthyl)-D,L-alanyl, 3-(2-naphthyl)-D,L-alanyl, 3-(2,4,6-trimethylphenyl)-D,L-alanyl, and 3-(4-trifluoromethylphenyl)-D,L-alanyl;

B is an amino acyl residue selected from the group consisting of D-phenylalanyl, D-p-Cl-phenylalanyl, D-p-F-phenylalanyl, D-p-nitrophenylalanyl, 3-(3,4,5-trimethoxyphenyl)-D-alanyl, 2,2-diphenylglycyl, D-α-methyl-p-Cl-phenylalanyl and 3-(2,4,6-trimethylphenyl)-D-alanyl;

C is an amino acyl residue selected from the group consisting of D-tryptophanyl, D-phenylalanyl, D-Me phenylalanyl, 3-(3-pyridyl)-D-alanyl, 3-(1-naphthyl)-D-alanyl, and 3-(2-naphthyl)-D-alanyl;

D is an amino acyl residue selected from the group consisting of L-seryl, and D-alanyl;

E is an amino acyl residue selected from the group consisting of L-phenylalanyl and L-tyrosyl;

F is an amino acyl selected from the group consisting of the radicals represented by the following structural formulas:

(a)

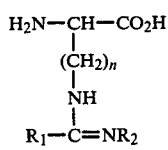

wherein n is 1 to 5;

$R_1$ is alkyl of 1 to 12 carbon atoms, $-NHR_3$ wherein $R_3$ is alkyl of 1 to 12 carbon atoms, cycloalkyl, phenyl, benzyl, morpholino or $-(CH_2)_n N(R_4)_2$ wherein n is 1 to 5 and $R_4$ is lower alkyl;

$R_2$ is hydrogen or $R_3$; or $R_1$ and $R_2$ comprise a ring represented by the following structural formulas:

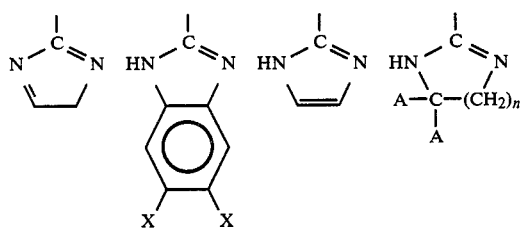

wherein n is 1 to 7; A is hydorgen, alkyl of 1 to 6 carbon atoms or cycloalkyl; and X is halo or A or (b)

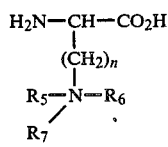

wherein $R_5$ is alkyl of 1 to 6 carbon atoms, benzyl, phenylethyl, cyclohexyl, cyclopentyl; and $R_6$ and $R_7$ are hydrogen or methyl; and n is the integer 2-5; or (c) a substituent of the formula

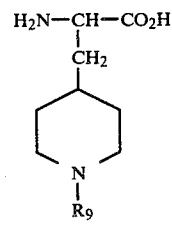

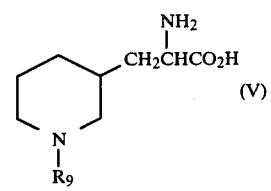

wherein $R_9$ is hydrogen, alkyl of 1 to 12 carbon atoms, phenyl or phenylloweralkyl;

G is an amino acyl residue selected from the group consisting of L-leucyl, L-norleucyl and L-norvalyl;

H is D-alaninamide, D-leucinamide, glycinamide or $-NHR_5$ wherein $R_5$ is lower alkyl or $NHCONH_2$.

3. A compound according to claim 1 or, claim 2 wherein F is N,N'-guanido-disubstituted-D-argininyl or D-homoargininyl.

4. The compound of claim 2 wherein A is N-Ac-L-Pro, N-Ac-D-Ser, N-Ac-D-p-Cl-Phe, N-Ac-D-Nal(2); B is D-p-F-Phe or D-p-Cl-Phe; C is D-Trp, D-Nal(2), D-3Pal or D-Phe; D is Ser; E is Tyr; F is the compound of Formula II wherein n is 3 or 4, $R_1$ is alkyl of 1 to 8 carbon atoms or cyclohexyl and $R_2$ is hydrogen, or a compound of Formula II wherein $R_1$ is $-NHR_3$ wherein $R_3$ is methyl, ethyl, n-propyl, isopropyl, n-hexyl or cyclohexyl and $R_2$ is $R_3$ or hydrogen, or F is a compound of formula II wherein $R_1$ and $R_2$ are dihydroim:dazolinyl or F is a compound of Formula (IV) or (V) wherein $R_9$ is hydrogen, methyl, pentyl or benzyl; and H is D-AlaNH$_2$, GlyNH$_2$ or NHEt.

5. The compound of claim 4 wherein A is N-Ac-L-Pro, N-Ac-D-Nal(2) or N-Ac-D-p-Cl-Phe, B is D-p-F-Phe or D-p-Cl-Phe, C is D-Nal(2), D-Trp, D-3Pal or D-Phe, D is Ser, E is Tyr, F is D-Dmh, D-Deh, D-Dph, D-Dhh or D-Dhi and H is D-AlaNH$_2$ GlyNH$_2$ or NHEt.

6. The compound of claim 5 which is N-Ac-L-Pro-D-p-F-Phe-D-Nal(2)-Ser-Tyr-F-Leu-Arg-Pro-GlyNH$_2$, wherein F is D-Dmh, D-Deh, D-Dph, D-Dhh, D-Dhi, D-Prh or D-Hha.

7. The compound of claim 5 which is N-Ac-L-Pro-D-p-Cl-Phe-D-Trp-Ser-Tyr-F-Leu-Arg-Pro-NHEt, wherein F is D-Dmh, D-Deh, D-Dph, D-Dhh, D-Dhi, D-Prh or D-Hha.

8. The compound of claim 5 which is N-Ac-D-p-Cl-Phe-D-p-Cl-Phe-D-Trp-Ser-Tyr-F-Leu-Arg-Pro-GlyNH$_2$, wherein F is D-Dmh, D-Deh, D-Dph, D-Dhi, D-Dhh, D-Prh or D-Hha.

9. The compound of claim 5 which is N-ac-D-Nal(2)-D-p-F-Phe-D-Trp-Ser-Tyr-F-Leu-Arg-Pro-GlyNH$_2$, wherein F is D-Dmh, D-Deh, D-Dph, D-Dhh, DDhi, D-Prh, D-Hha or propyl amidine.

10. The compound of claim 5 which is N-Ac-D-p-Cl-Phe-D-p-Cl-Phe-D-Trp-Ser-Tyr-F-Leu-Arg-Pro-D-AlaNH$_2$, wherein F is D-Dmh, D-Deh, D-Dph, D-Dhi, D-Dhh, D-Drh or D-Hha.

11. The compound of claim 5 which is N-Ac-D-Nal(2)-D-p-Cl-Phe-D-Trp-Ser-Tyr-F-Leu-Arg-Pro-D-AlaNH$_2$, wherein F is D-Dmh, D-Deh, D-Dph, D-Dhh or D-Dhi.

12. A pharmaceutical composition useful as an LHRH antagonist comprising an effective amount of the compound of claim 1 in admixture with at least one pharmaceutically acceptable excipient.

* * * * *